(12) United States Patent
Wang et al.

(10) Patent No.: US 12,053,325 B2
(45) Date of Patent: Aug. 6, 2024

(54) CROSS-RAY ULTRASOUND TOMOGRAPHY (CRUST) METHODS AND SYSTEMS

(71) Applicant: California Institute of Technology, Pasadena, CA (US)

(72) Inventors: Lihong Wang, Arcadia, CA (US); Shuai Na, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 405 days.

(21) Appl. No.: 17/248,048

(22) Filed: Jan. 6, 2021

(65) Prior Publication Data

US 2021/0204909 A1 Jul. 8, 2021

Related U.S. Application Data

(60) Provisional application No. 62/957,502, filed on Jan. 6, 2020.

(51) Int. Cl.
| | |
|---|---|
| *A61B 8/15* | (2006.01) |
| *A61B 8/00* | (2006.01) |
| *A61B 8/06* | (2006.01) |
| *A61B 8/08* | (2006.01) |

(52) U.S. Cl.
CPC .................. *A61B 8/15* (2013.01); *A61B 8/06* (2013.01); *A61B 8/4483* (2013.01); *A61B 8/488* (2013.01)

(58) Field of Classification Search
CPC ........... A61B 8/15; A61B 8/448; A61B 8/488; G01S 15/8913
See application file for complete search history.

(56) References Cited

U.S. PATENT DOCUMENTS

| | | | | |
|---|---|---|---|---|
| 4,474,065 | A * | 10/1984 | Miessler | B06B 1/0622 73/628 |
| 4,630,612 | A * | 12/1986 | Uchida | A61B 8/06 600/455 |
| 10,226,234 | B2 * | 3/2019 | Specht | G01S 15/8984 |
| 2001/0031922 | A1 * | 10/2001 | Weng | A61B 8/4461 601/3 |
| 2002/0169378 | A1 * | 11/2002 | Mo | G01S 7/52084 600/437 |

(Continued)

OTHER PUBLICATIONS

Clement. Portable Ultrasound Imaging of the Brain for Use in Forward Battlefield Areas. U.S. Army Medical Research and Materiel Command (2011) (Year: 2011).*

(Continued)

*Primary Examiner* — Angela M Hoffa
*Assistant Examiner* — Younhee Choi
(74) *Attorney, Agent, or Firm* — Sheila Martinez-Lemke; Weaver Austin Villeneuve & Sampson LLP

(57) ABSTRACT

Among the various aspects described herein is the provision of systems and methods of cross-ray ultrasound tomography. In some embodiments, a cross-ray ultrasound tomography system utilizes an ultrasonic emitter configured to emit one or more ultrasonic waves and an ultrasonic detector array configured to generate one or more radio frequency signals in response to detecting ultrasonic waves. The ultrasonic emitter and the ultrasonic detector array are configured such that the one or more ultrasonic waves are emitted by the ultrasonic emitter at an angle to a focal plane of the ultrasonic detector array.

20 Claims, 14 Drawing Sheets

(56) References Cited

U.S. PATENT DOCUMENTS

2006/0287596 A1* 12/2006 Johnson ............... A61B 8/0825
  600/437
2017/0055950 A1* 3/2017 Matsuda .............. A61B 8/4488
2017/0156704 A1* 6/2017 Flynn .................. G01S 15/8995

OTHER PUBLICATIONS

Thotakura. Simulation of Ultrasound Computed Tomography in Diffraction Mode. Thesis submitted to Ottawa-Carleton Institute for Biomedical Engineering. 2014 (Year: 2014).*

Xu, M and L.V. Wang, "Universal back-projection algorithm for photoacoustic computed tomography", Physical Review E., (Jan. 19, 2005); 71(1):016706.

Xu, M and L.V. Wang, "Analytic explanation of spatial resolution related to bandwidth and detector aperture size in thermoacoustic or photoacoustic reconstruction", Physical Review E., (May 9, 2003), 67(5):056605.

Demené, C. et al., "Spatiotemporal clutter filtering of ultrafast ultrasound data highly increases Doppler and fUltrasound sensitivity", IEEE transactions on medical imaging, (Apr. 30, 2015), 34(11):2271-85.

* cited by examiner

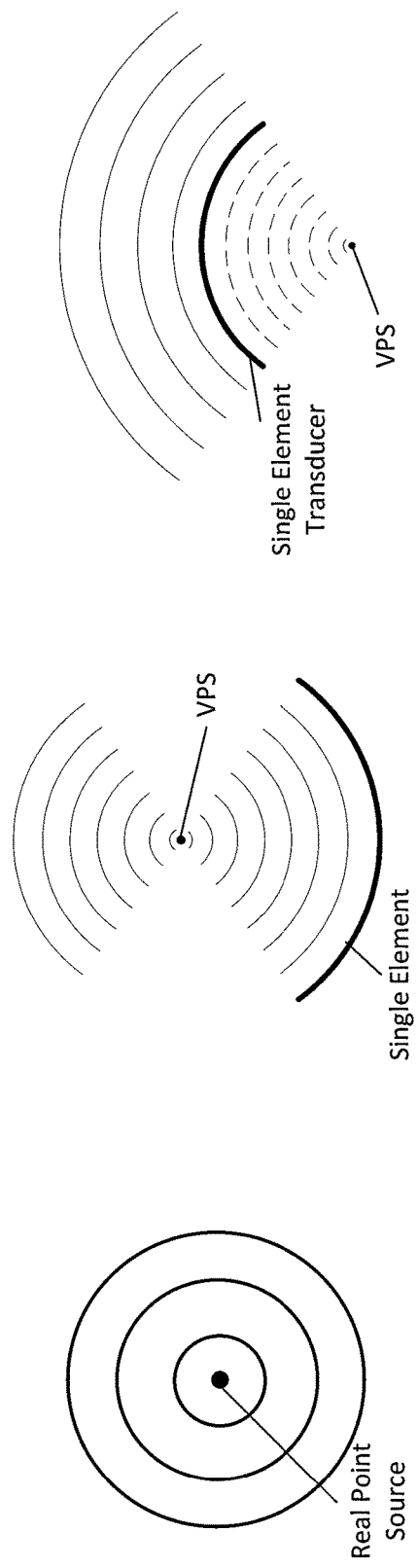
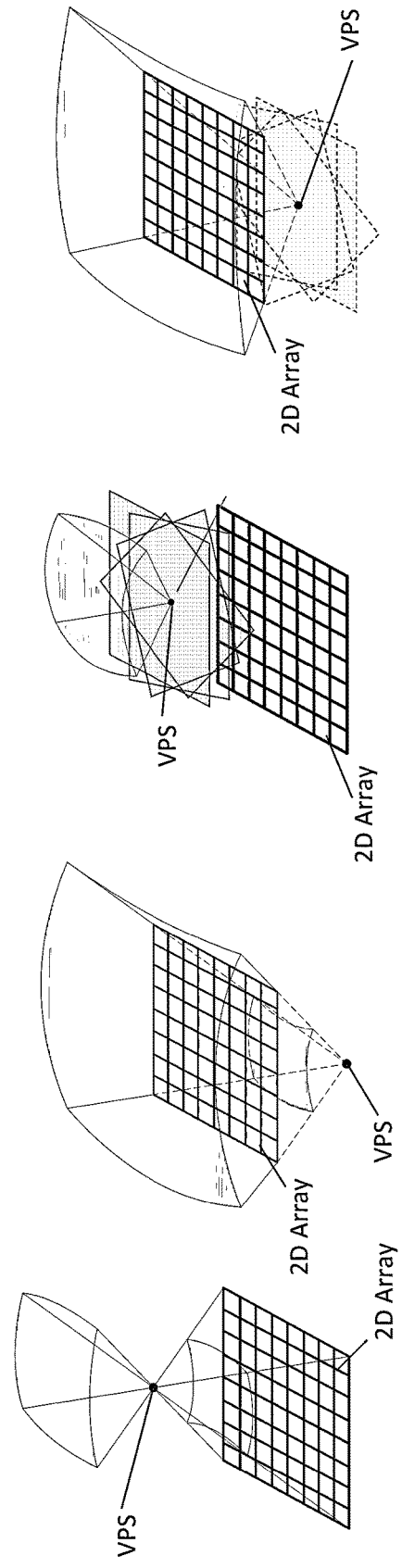
FIG. 3A
FIG. 3B
FIG. 3C
FIG. 3D
FIG. 3E
FIG. 3F
FIG. 3G

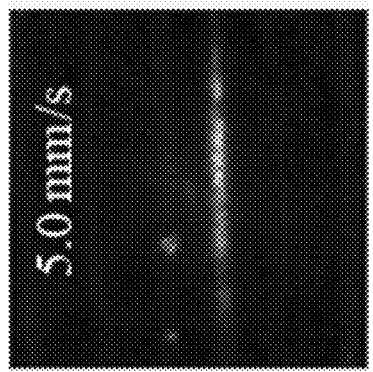
FIG. 12B
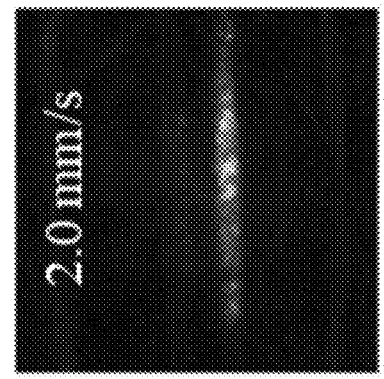
FIG. 12D
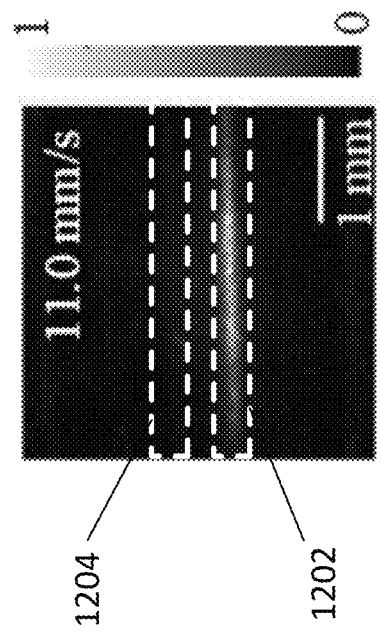
FIG. 12A
FIG. 12C

CROSS-RAY ULTRASOUND TOMOGRAPHY (CRUST) METHODS AND SYSTEMS

CROSS-REFERENCES TO RELATED APPLICATIONS

This application claims priority to and benefit of U.S. Provisional Patent Application No. 62/957,502, titled "Cross-Ray Ultrasound Tomography (CRUST)" and filed on Jan. 6, 2020, which is hereby incorporated by reference in its entirety and for all purposes.

FIELD

Certain embodiments generally relate to ultrasound tomography, and specifically, certain embodiments relate to cross-ray ultrasound tomography methods and systems.

BACKGROUND

Ultrasound imaging emits ultrasonic pulses and detects the ultrasonic echoes reflected or scattered by tissues or other materials. Unlike radiography or nuclear-medicine-based imaging methods, ultrasound imaging involves no ionizing radiation. Conventional ultrasound techniques scan the region of interest (ROI) line by line with a focused beam. Therefore, conventional ultrasound is too slow to acquire large-field images of centimeters scale at a kHz frame rate, which is critical for measuring blood dynamics. Consequently, imaging blood dynamics by conventional ultrasound requires dividing the imaging field into smaller sub-regions.

Additionally, conventional ultrasound is limited to the estimation of the flow velocity component along the beam axis. In contrast, plane-wave-based ultrafast ultrasound imaging allows for large-field imaging using only a few tilted planar excitations. Coherently summing the resulting set of images, one can produce a high-resolution ultrasound image, referred to as a 'compound' image, with a trade-off between the frame rate, contrast, and resolution. Nevertheless, plane-wave-based ultrafast Doppler imaging also suffers from low sensitivity to flows or motions perpendicular to the acoustic axis of the transducer array. Thus, existing Doppler ultrasound imaging techniques are fundamentally limited in sensitivity along the directions perpendicular to or away from the transducer axis.

SUMMARY

Certain aspects pertain to methods and systems for cross-ray ultrasound tomography.

Certain aspects pertain to a cross-ray ultrasound tomography system. In one implementation, the cross-ray ultrasound tomography system includes: an ultrasonic emitter configured to emit one or more ultrasonic waves; an ultrasonic detector array configured to generate one or more radio frequency signals in response to detecting ultrasonic waves, wherein the ultrasonic emitter and the ultrasonic detector array are configured such that the one or more ultrasonic waves are emitted by the ultrasonic emitter at an angle to a focal plane of the ultrasonic detector array; and a computing device configured to: calculate a scattering coefficient at each of a plurality of spatial coordinates, wherein the scattering coefficient at each spatial coordinate is calculated using digitized acoustic data based on the one or more radio frequency signals generated by the ultrasonic detector array; and construct one or more tomographic images from the scattering coefficients calculated at the plurality of spatial coordinates.

Certain aspects pertain to a cross-ray ultrasound tomography method. In one implementation, the cross-ray ultrasound tomography method includes: causing one or more ultrasonic waves to be emitted by an ultrasonic emitter in a direction at an angle to a focal plane of an ultrasonic detector array; digitizing one or more radio frequency signals generated by the ultrasonic detector array to generate digitized acoustic data; and forming one or more tomographic images by calculating a scattering coefficient at each of a plurality of spatial coordinates using the digitized acoustic data.

Certain aspects pertain to a method for generating power Doppler images and/or quantifying flow velocity. In one implementation, the method for generating power Doppler images and/or quantifying flow velocity includes: identifying a point source location associated with an ultrasonic emitter and a plurality of locations for a plurality of ultrasonic detectors, wherein the ultrasonic emitter and the plurality of ultrasonic detectors are configured such that ultrasonic waves are emitted in a direction at an angle to a direction from which ultrasonic waves are detected; causing ultrasonic signals to be emitted by the ultrasonic emitter; digitizing one or more radio frequency signals generated by the plurality of ultrasonic detectors; constructing a plurality of frames of tomographic images based on the digitized radio frequency signals; clutter filtering the plurality of frames of tomographic images; calculating amplitude and temporal frequency at each of a plurality of pixels of each frame in the clutter-filtered plurality of frames of tomographic images; calculating a Doppler frequency shift at each of the plurality of pixels based on the amplitude and temporal frequency calculated at each pixel in the clutter-filtered plurality of frames of tomographic images; and calculating a flow velocity vector at each of the plurality of pixels based on the Doppler frequency shift calculated at each of the plurality of pixels.

These and other features are described in more detail below with reference to the associated drawings.

BRIEF DESCRIPTION OF THE DRAWINGS

FIGS. 3A-3L are schematic drawings of various configurations of ultrasonic emitters and/or ultrasonic detector arrays in accordance with some embodiments.

FIGS. 12A-12H illustrate experimental results obtained from using a CRUST system for power Doppler imaging, according to an aspect.

Figure 1:
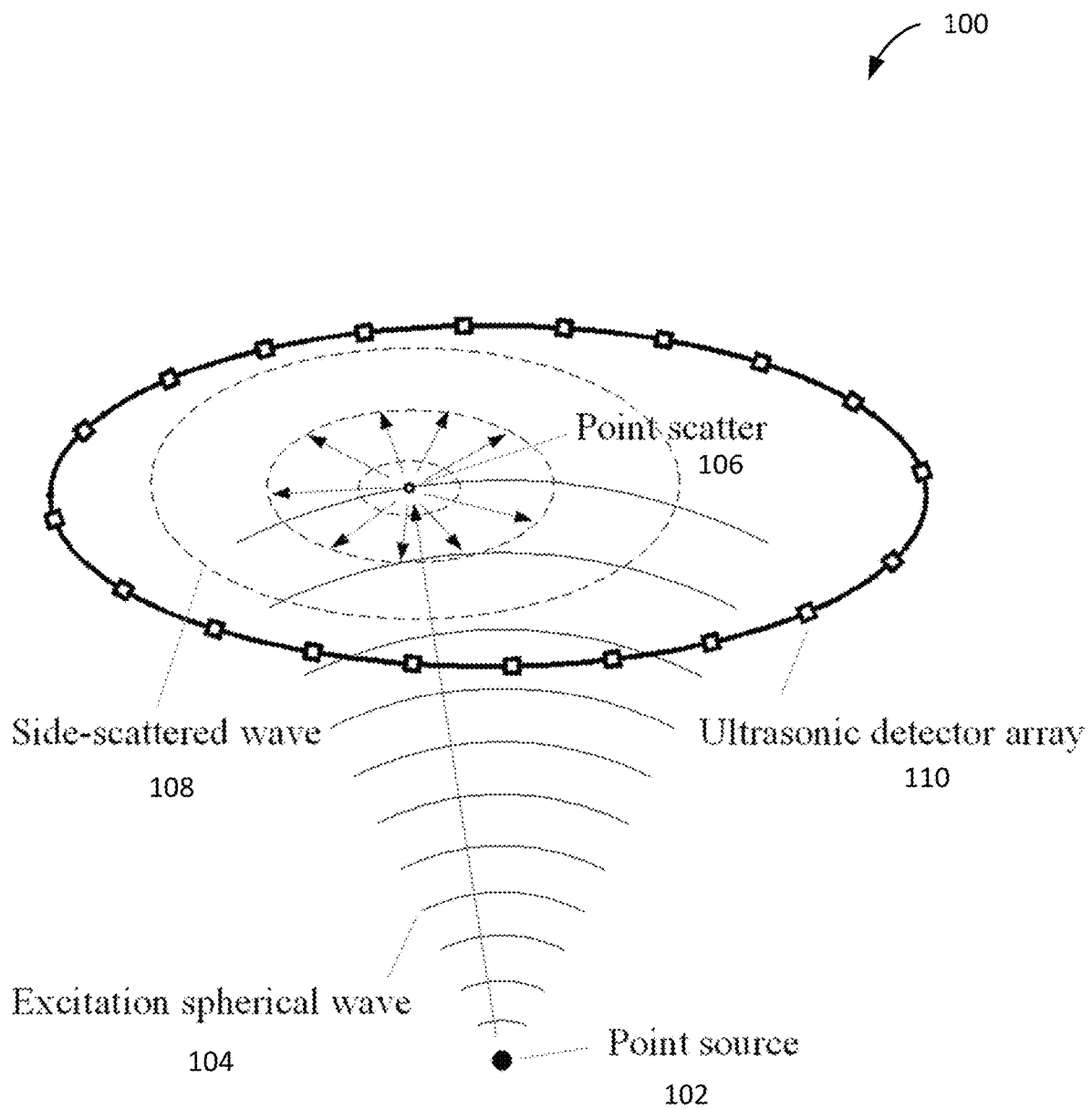
FIG. 1 is a schematic diagram of propagation of and detection of ultrasonic waves in accordance with some embodiments.

These and other features are described in more detail below with reference to the associated drawings.

DETAILED DESCRIPTION

Different aspects are described below with reference to the accompanying drawings. The features illustrated in the drawings may not be to scale. In the following description, numerous specific details are set forth in order to provide a thorough understanding of the presented embodiments. The disclosed embodiments may be practiced without one or more of these specific details. In other instances, well-known operations have not been described in detail to avoid unnecessarily obscuring the disclosed embodiments. While the disclosed embodiments will be described in conjunction with the specific embodiments, it will be understood that it is not intended to limit the disclosed embodiments. Certain aspects pertain to cross-ray ultrasound tomography (CRUST) systems and methods, which can be used, for example, to obtain ultrasound images of structures, to measure fluid flow such as blood flow in vessels, etc.

I. Introduction

The present disclosure sets forth systems and methods that implement Cross-Ray Ultrasound Tomography (CRUST). These CRUST methods and systems can be used to perform, e.g., high-resolution large-field ultrasound imaging. Alternatively or additionally, these CRUST systems and methods can be used, e.g., to measure angle-independent flows or motions.

In certain aspects, CRUST systems are ultrasound systems with an ultrasonic emitter (sometimes referred to herein as an "ultrasonic transmitter" or "ultrasonic transmitters") that is physically separate from an ultrasonic detector array. This configuration provides that at least one of the transmitted and received rays has a non-zero dot product with any non-zero flow vector. Accordingly, these CRUST systems may be configured to be sensitive to flows and/or motions in any or all directions. By contrast, conventional ultrasound imaging cannot detect flows perpendicular to the acoustic axis since both transmit and receive rays have a zero dot product with the flow vector.

Moreover, because these CRUST systems utilize an independent ultrasonic emitter to send excitation rays into the field of view (FOV), images may be formed at the same frame rate as the emission rate. By contrast, conventional ultrasound computed tomography systems transmit ultrasound beams from all transducer elements sequentially and each transducer element receives the echoes from other or the same element simultaneously, thereby limiting the imaging frame rate by the number of transmit events required to form a single frame. The frame rate of CRUST systems may instead only be limited by the single-trip time of flight (TOF) of ultrasound in the FOV. In particular, a CRUST system can reconstruct an image using a single transmit event, whereas conventional ultrasound systems may need to use many transmit events to reconstruct an image. Accordingly, the frame rate of certain CRUST systems may be as high as 30 kHz for a 5-cm FOV in, for example, biological tissue.

By utilizing an independent ultrasonic emitter and ultrasonic detector array configuration, certain CRUST systems may be used to generate tomographic images with both high spatial resolution along an axis perpendicular to transmission axis, as well as high temporal resolution. For example, a CRUST system of 5 MHz center ultrasonic frequency can provide a resolution of ~125 μm and frame rate as high as 30 KHz for a 5-cm FOV in biological tissues. Such resolution and frame rate are sufficient for applications of heart and brain imaging of small animals or humans. In general, CRUST systems may be suitable for structural imaging, power doppler imaging (PDI), and vector flow estimation. For example, CRUST systems can be used for imaging of various tissues or organs, blood flow velocity estimation in blood vessels of heart, brain, liver, etc.

II. Cross-Ray Ultrasound Tomography (CRUST)

FIG. 1 shows a schematic diagram that illustrates the imaging principle of a CRUST technique in accordance with some embodiments. The CRUST technique is being implemented by a CRUST system 100 having an ultrasonic emitter having a point source 102 and an ultrasonic detector array 110. Although the ultrasonic emitter is illustrated as having a single point source 102, the target (also sometimes referred to herein as a "sample") is shown as having a point scatter target 106, and the ultrasonic detector array 110 is shown as having a circular arrangement of twenty (20) ultrasonic transducers, it would be understood that the disclosure is not so limited. Other numbers of elements and arrangements may be implemented in other examples. The illustrated example is shown during an instant of time when the point scatter target 106 is being imaged during operation of the CRUST system 100.

As illustrated, the CRUST system 100 includes a point source 102 that can generate an excitation spherical wave 104 for, e.g., wide-field excitation. Point source 102 can be either a physical point source, or a virtual point source (VPS). A physical point source can be any ultrasonic emitter (e.g., transducer) that has a small physical emitting aperture relative to the ultrasound wavelength, as discussed in more detail in connection with FIG. 3A. By contrast, a VPS can refer to a focal point of an ultrasonic emitter such as a single transducer or an array of ultrasonic transducers that is not co-located with the ultrasonic detector array. An example of a single element spherically focused transducer and an associated virtual point source is described with reference to FIG. 5. Some examples of physical and virtual point sources are also shown in and discussed further in connection with FIGS. 3A-3G.

It should be noted that an ultrasonic emitter as used herein can include a single element transducer or an array of transducers.

The point scatter target 106 may cause scattering of the excitation spherical wave 104 to generate side-scattered waves. In the illustrated example, excitation spherical wave 104 generates side-scattered waves 108 due to scattering from point scatter target 106.

The side-scattered wave(s) 108 can be detected by one or more of the ultrasonic detectors (e.g., ultrasonic transducers) included in ultrasonic detector array 110. As shown in FIG. 1, ultrasonic detector array 110 is physically separate from point source 102 of the ultrasonic emitter. Additionally, because ultrasonic detector array 110 detects ultrasonic waves using elements that are different from those used to generate the excitation spherical wave 104, ultrasonic detector array 110 is independent from an ultrasonic emitter associated with point source 102 in that ultrasonic detector array 110 can detect ultrasonic waves simultaneously with or concurrent with emission of ultrasonic waves by the ultrasonic emitter associated with point source 102.

Figure 5:
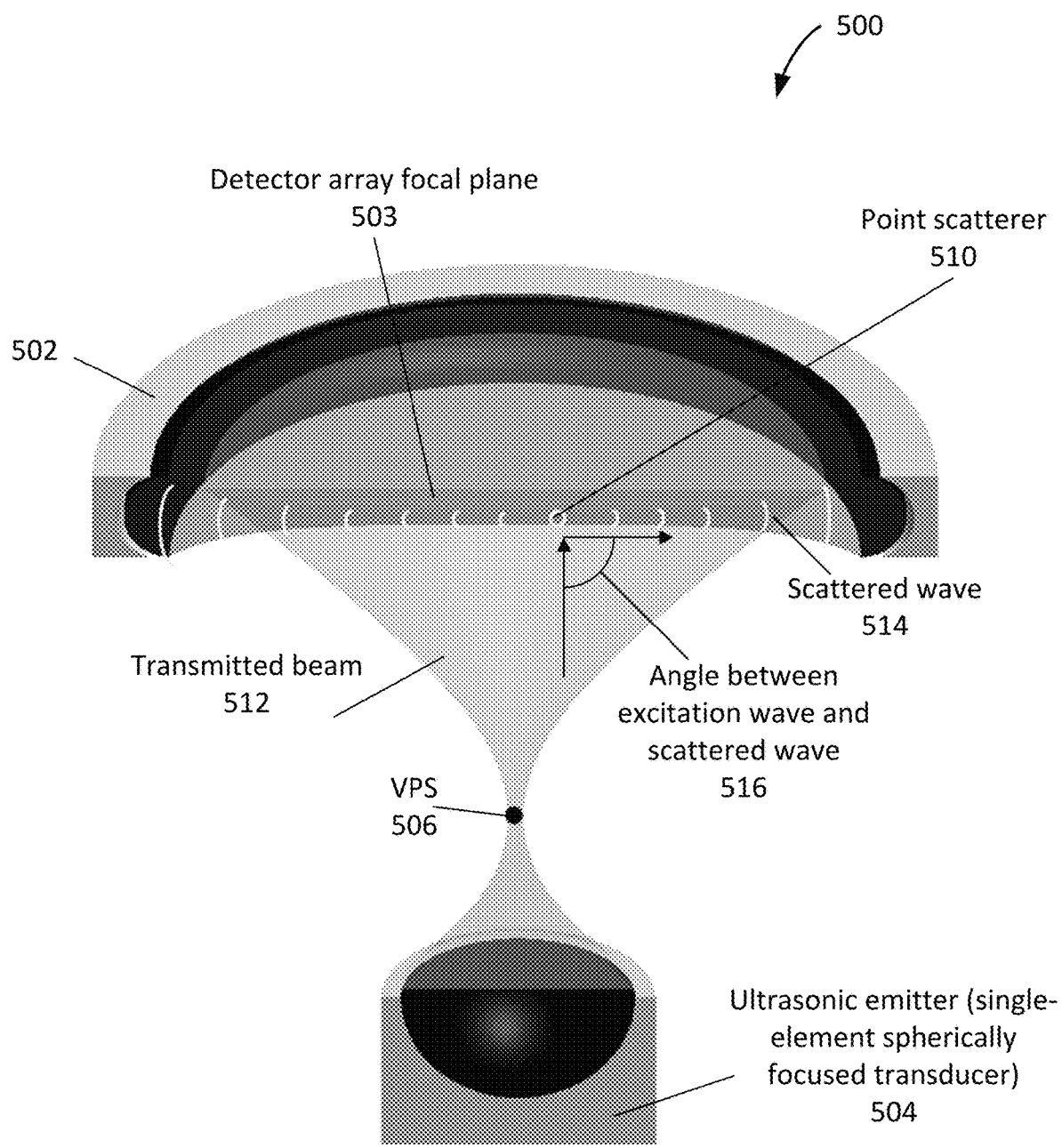
FIG. 5 is a schematic diagram of one implementation of an ultrasonic emitter and an ultrasonic detector array of a CRUST system in accordance with some embodiments.

In the illustrated CRUST system, ultrasonic detector array 110 and point source 102 are configured (e.g., located) such that excitation spherical wave 104 and side-scattered wave 108 cross. That is, excitation spherical wave 104 and side-scattered wave 108 cross in that at least one ray of excitation spherical wave 104 and at least one ray of side-scattered wave 108 are propagated at an angle to each other such that the dot product of the excitation ray and the side-scattered ray is non-zero. In other words, excitation spherical wave 104 and side-scattered wave 108 are not propagated in parallel. For example, point source 102 may be located to emit an excitation spherical wave that propagates at an angle to the focal plane of ultrasonic detector array 110. As a more particular example, the excitation spherical wave may propagate at an angle to the focal plane within a range of about 60 degrees to about 120 degrees, within a range from about 70 degrees to about 110 degrees, within a range from about 80 degrees to about 100 degrees, etc. An example of an angle of an excitation spherical wave to a detector focal plane is shown in FIG. 5.

Figure 2A:
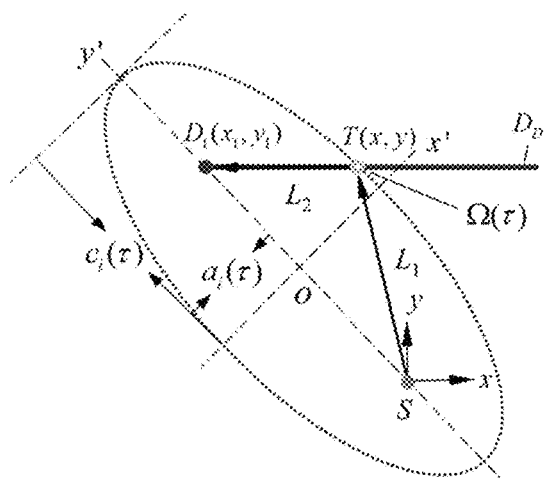
FIGS. 2A-2C depict schematic diagrams of points of interest for calculation scattering coefficients for 1-D case, 2-D case, and 3-D case respectively, in accordance with some embodiments.
Figure 2B:
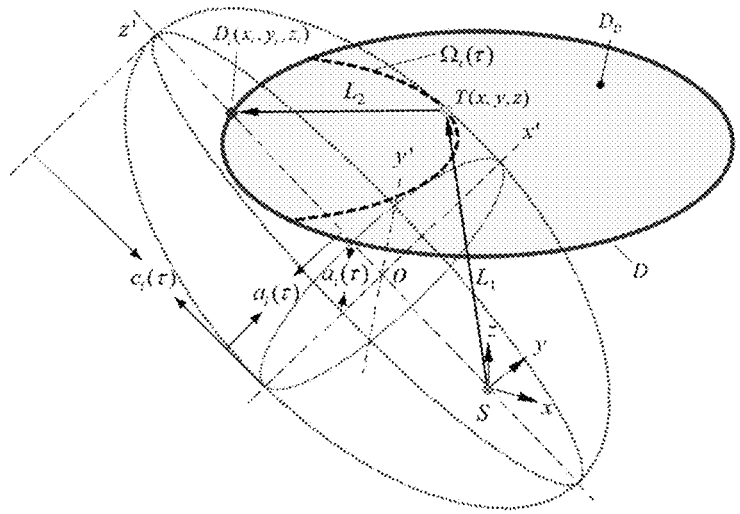
Figure 2C:
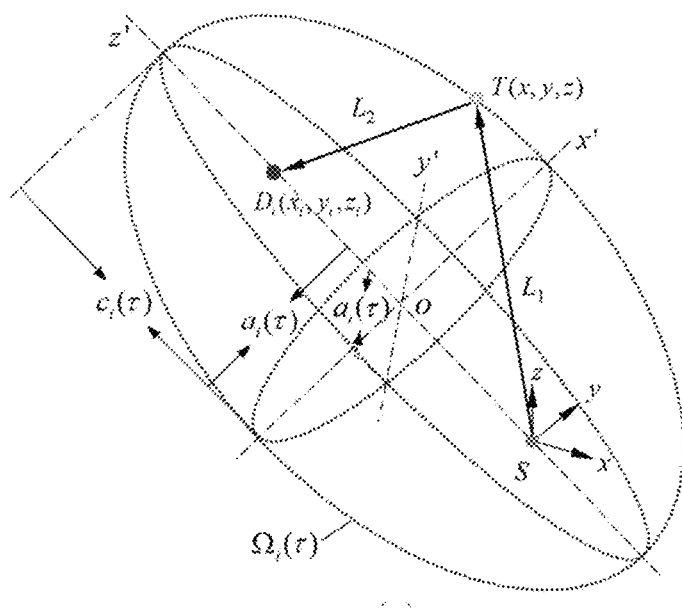

FIGS. 2A-2C show schematic diagrams that may be used to derive a relationship between the detected pressure at the detectors in an ultrasonic detector array of a CRUST system and the scattered pressure from a target in accordance with some embodiments. In particular, FIGS. 2A-2C illustrate the use of an ellipsoidal Radon transform. Note that FIG. 2A shows a 1-D detection case, FIG. 2B shows a 2-D detection case, and FIG. 2C shows a general 3-D detection case.

In FIGS. 2A-2C, a global coordinate system is defined with a point source S of an ultrasonic emitter as the origin, a point scatter target located at (x, y, z) is denoted as T, a detection geometry of the ultrasonic detection array is denoted as D, the $i^{th}$ detector on D is denoted as $D_i(x_i, y_i, z_i)$, and the detection domain of the detectors is denoted as $D_D$. Note that, for the 1-D case shown in FIG. 2A, the third dimension along z is ignored. Additionally, note that in FIG. 2C, the 3-D detection geometry D, which can be arbitrarily as long as it encloses T, is omitted for readability.

The distance between the point scatter target T and the point source S can be defined as $L_1$, and the distance between the point scatter target T and the $i^{th}$ detector $D_i$ can be defined as $L_2$. The total ultrasound time of flight along $L_1$ and $L_2$ can be defined as $\tau$. Therefore, at a given $\tau$ and speed of sound (SOS) c, the sum of $L_1$ and $L_2$ can be defined as: c*$\tau$.

For the 1-D case shown in FIG. 2A, the position of the point scatter target T is at an intersection point $\Omega(\tau)$ of the detection domain $D_D$ and an ellipse with the point source S and detector $D_1$ as the focal points. For the 2-D case shown in FIG. 2B, the possible distribution of point scatter target T yields the partial intersecting ellipse $\Omega_i(\tau)$ of an ellipsoid with two equal semi-diameters (spheroid) and the detection domain $D_D$. For the 3-D case shown in FIG. 2C, the possible distribution of point scatter target T yields a spheroid $\Omega_i(\tau)$.

Without loss of generality, the ellipsoidal Radon transform is described below for the more general 3-D case. It would be understood that a similar methodology may apply to the 1-D and 2-D cases.

The ellipsoid $\Omega_i(\tau)$ in FIG. 2C can be expressed as:

$$\frac{1}{a_i(\tau)^2}\left(x^2 + y^2 + z^2 - \frac{(xx_i + yy_i + zz_i)^2}{sD_i^2}\right) + \quad \text{(Eqn. 1)}$$

-continued
$$\frac{1}{c_i(\tau)^2}\left(\frac{xx_i + yy_i + zz_i}{sD_i} - \frac{SD_i}{2}\right)^2 = 1$$

In equation 1 above, $TD_i$ represents the distance between $i^{th}$ detector $D_i$ and point scatter target T, $a_i(\tau)=\sqrt{(c\tau)^2-SD_i^2}/4$ denotes the equatorial radius of the ellipsoid, and $c_i(\tau)=c\tau/2$ stands for the distance from the center to the pole along the symmetry axis. If the long axis is aligned with the z axis and the equator is aligned with the x-y plane, equation 1 is reduced to the following:

$$\frac{x^2}{a_i(\tau)^2} + \frac{y^2}{a_i(\tau)^2} + \frac{z^2}{c_i(\tau)^2} = 1 \quad \text{(Eqn. 2)}$$

In an ideal case of certain aspects where the electric impulse responses or EIRs of the ultrasonic emitter and ultrasonic detector array have infinite bandwidths, the emitter input is a Delta function, and the scattering is isotropic, the detected pressure signal at the $i^{th}$ detector $D_i$ can be written as an ellipsoidal Radon transform of the scattering coefficient:

$$R_i(\varepsilon)(t) = \frac{1}{4\pi c^2}\int \frac{\varepsilon(x, y, z)}{L_2}\frac{P_0}{L_1}\frac{\partial}{\partial t}\delta(t - \tau)dxdydz \quad \text{(Eqn. 3)}$$

In equation 3 above, $\varepsilon(x, y, z)$ represents the scattering coefficient, $P_0$ is related to the source amplitude, and $P_0L_1$ represents the excitation pressure amplitude at (x, y, z). The universal back-projection (UBP) technique can be extended to estimate the inverse ellipsoidal Radon transform of equation 3. A discussion of the UBP technique can be found in, for example, Minghua Xu, and Lihong V. Wang. "Universal back-projection algorithm for photoacoustic computed tomography." Physical Review E, 71.1(2005): 016706, which is incorporated by reference herein in its entirety.

By extending the UBP technique, a discrete approximation of the inverse ellipsoidal Radon transform of equation 3 can be expressed as:

$$\varepsilon(x, y, z) = \quad \text{(Eqn. 4)}$$
$$\frac{1}{\sum_{i=1}^{N}\psi_i(x, y, z)}\sum_{i=1}^{N}\left[\left(2RF_i(\tau) - 2t\frac{\partial RF_i(t)}{\partial t}\bigg|_{t=\tau}\right)x\psi_i(x, y, z)\right]$$

In equation 4 above, $RF_i$ denotes the radio-frequency (RF) signals detected by the $i^{th}$ detector $D_i$, N stands for the total number of detectors on the ultrasonic detection array D, and $\psi_i(x, y, z)$ represents the solid angle for the $i^{th}$ detector $D_i$ with respect to the point source S.

The second term in the summation of equation 4 is usually much larger than the first term. However, because the derivative represents a ramp filter, which in practice is similar to the electric impulse response of the $i^{th}$ detector, equation 4 may be simplified to:

$$\varepsilon(x, y, z) \approx \frac{1}{\sum_{i=1}^{N}\psi_i(x, y, z)}\sum_{i=1}^{N}[(2RF_i(\tau)\tau)\times\psi_i(x, y, z)] \quad \text{(Eqn. 5)}$$

Where ε(x, y, z) represents the scattering coefficient at spatial coordinates, $\psi_i$(x, y, z) represents the solid angle for the $i^{th}$ detector $D_i$ with respect to the point source S, and $RF_i$ represents the radio-frequency (RF) signals detected by the $i^{th}$ detector $D_i$. Although Equation 5 is described with respect to implementation in CRUST systems, it may also be implemented as a beamforming algorithm in commercially available ultrasound imaging systems.

III. Cross-Ray Ultrasound Tomography (CRUST) Systems

Generally speaking, CRUST techniques involve ultrasound-imaging that uses a spherical acoustic wave for wide-field excitation (in contrast to focused excitation) and cross-axis detectors for signal detection. The size of a field of view (FOV) of a CRUST system is dependent on the distance between the focal point of the ultrasound emitter (transducer) (i.e., the VPS) and the detection field of the detector array. Taking the ultrasound emitter (transducer) A3085-SU (5 MHz central frequency, Olympus, Corp.) as an example, the diameter of the FOV is about 1 cm when the focal point of the ultrasound emitter (transducer) (i.e., the VPS) is at a distance of 1.1 cm from the detection field. When the distance between the focal point of the ultrasound emitter (transducer) (i.e., the VPS) and the detection field is 5 cm, the diameter of the FOV will be 5.5 cm.

CRUST techniques may be implemented in systems (generally referred to herein as "CRUST systems") having various configurations of ultrasonic emitters and ultrasonic detectors.

In certain aspects, a CRUST system includes an ultrasonic emitter that is configured to emit acoustic spherical waves into a medium, such as biological tissue and/or an acoustic medium within which the biological tissue is positioned. The ultrasonic emitter may be a single transducer element or an array of transducer elements. The CRUST system can additionally include an ultrasonic detector array that has one or more ultrasonic detectors (e.g., two, three, ten, twenty, etc.). Each ultrasonic detector (ultrasonic transducer) can be configured to generate one or more radio frequency (RF) signals in response to detecting ultrasonic waves that are for example, scattered from a target in the medium. In other words, each ultrasonic detector can be configured to convert a detected ultrasonic wave to RF signals that can be recorded.

The ultrasonic detector array can be independent in operation from the ultrasonic emitter (which may be a single element transducer or an array of transducer elements). That is, in some implementations, each element of the ultrasonic detector array can detect ultrasonic waves and generate RF signals simultaneously with the waves emitted by the ultrasonic emitter. Additionally, the ultrasonic detector array can be physically separate from the ultrasonic emitter. In particular, the ultrasonic emitter and the ultrasonic detector array can be placed in locations such that a path of waves detected by the ultrasonic detector array crosses a path of spherical waves emitted by the ultrasonic emitter. In some embodiments, a CRUST system is configured so that the path of detected waves cross the path of emitted waves by locating the ultrasonic emitter such that a point source associated with the ultrasonic emitter is at an angle to a focal plane of the ultrasonic detector array. As a more particular example, the excitation spherical wave may propagate at an angle within a range of about 60 degrees to about 120 degrees, within a range from about 70 degrees to about 110 degrees, within a range from about 80 degrees to about 100 degrees, etc.

In certain aspects, a CRUST system includes an ultrasonic emitter with at least one point source (e.g., a focal point of an ultrasonic transducer) configured for ultrasonic transmission of one or more spherical acoustic waves. The point source may be either a physical point source (sometimes referred to herein as a "real point source") or a virtual point source (VPS). Note that point source S shown in FIGS. 2A-2C and denoted in equations 1-5 above may correspond to either a physical point source or a VPS. A "physical point source" or "real point source" can refer to an ultrasonic transducer that has a small physical emitting aperture relative to the ultrasound wavelength. A "virtual point source" can refer to a focal point of an ultrasonic emitter (e.g., single element transducer or an array of ultrasonic transducers) that is not co-located with the ultrasonic transducers of the detector array.

A VPS may be used in some embodiments, for example, when the output power of a physical point source of the ultrasonic emitter is limited by, e.g., the small aperture size of the transducer element(s). By contrast, a VPS may generate a higher power output and can be readily implemented using one or more ultrasonic transducers or ultrasonic transducer arrays. A VPS can be implemented using either "positive focusing" or "negative focusing," where positive focusing or negative focusing indicates a location of a focal point, which corresponds to the location of the VPS, relative to the ultrasonic transducers of the ultrasonic emitters. In particular, positive focusing indicates that the focal point, and therefore, the VPS, is located in a direction in which the spherical wave propagates from the ultrasonic emitter(s). Conversely, negative focusing indicates that the focal point, and therefore, the VPS, is located in a direction opposite from which the spherical wave propagates from the ultrasonic emitter(s).

FIGS. 3A-3L depict various examples of ultrasonic emitters configurations and ultrasonic detector array configurations for CRUST systems in accordance with some embodiments. In particular, FIGS. 3A-3G illustrate various configurations of ultrasonic emitters.

An example of an ultrasonic emitter configuration with a real point source is shown in FIG. 3A. In some embodiments, a physical point source may be a photoacoustic-based passive absorber or a single element ultrasonic transducer that has a diameter much less than the acoustic wavelength. For example, if the CRUST system has an ultrasound central frequency of 5 MHz with water as coupling medium, the acoustic wavelength is about 300 μm and the point source size should be smaller than 300 μm. Although a larger point source, which can generate a higher acoustic power in general, can also be used, the spatial resolution of the CRUST system may degrade.

Examples of ultrasonic emitters with a VPS implemented using a single-element ultrasonic transducer are shown in FIG. 3B and FIG. 3C. In FIG. 3B, the ultrasonic emitter incudes a VPS implemented using a single-element transducer with positive focusing. In some embodiments, positive focusing can be achieved using a single-element ultrasonic transducer that is convex in shape. In FIG. 3C, the ultrasonic emitter incudes a VPS implemented using a single-element transducer with negative focusing. In some embodiments, negative focusing can be achieved using a single-element ultrasonic transducer that is concave in shape. Examples of single element transducers that can be used as emitters in a CRUST system include A395S-SU (2.25 MHz central frequency) and A3085-SU (5 MHz central frequency) from Olympus, Corp.

Examples of ultrasonic emitters having a VPS implemented using two-dimensional arrays of ultrasonic transducers are shown in FIGS. 3D-3G. FIGS. 3D and 3E illustrate examples of ultrasonic emitters having positive and negative focusing, respectively, using a transmit beamforming technique implemented by a two-dimensional array of ultrasonic transducers. FIGS. 3D and 3E illustrate examples of ultrasonic emitters having positive and negative focusing, respectively, using multiple numerically synthesized plane waves. Note that VPS achieved using two-dimensional arrays can allow for fast electronic scan of the VPS relative to using a single-element transducer.

Figure 3H:
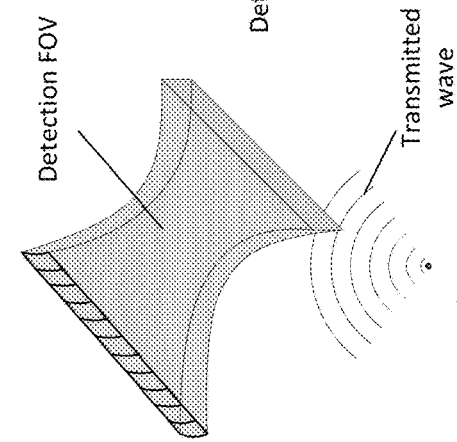
Figure 3I:
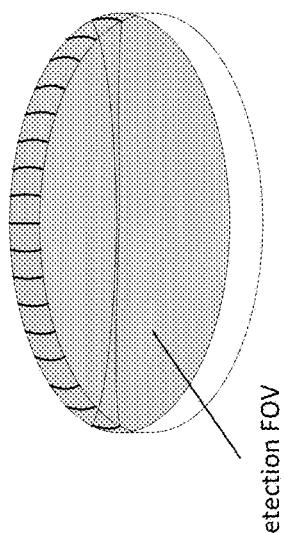
Figure 3J:
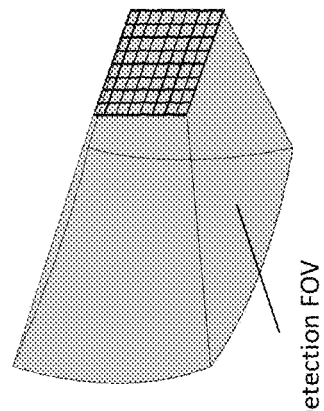
Figure 3K:
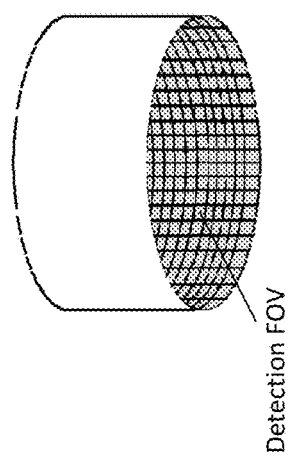
Figure 3L:
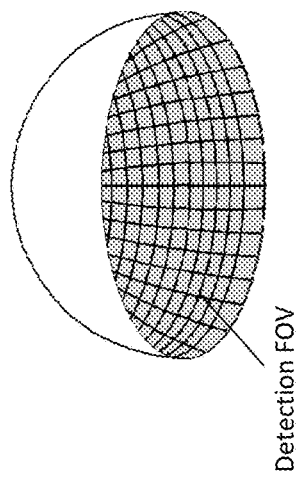

FIGS. 3H-3L illustrate various configurations of ultrasonic detector arrays that can be used in a CRUST system. FIGS. 3H and 3 illustrate 1-D ultrasonic detector arrays that can be used for 2-D imaging. In particular, FIG. 3H illustrates a linear ultrasonic detector array and FIG. 3I illustrates a full ring ultrasonic detector array. FIGS. 3J-3L illustrate 2-D ultrasonic detector arrays that can be used for 3-D imaging. In particular, FIG. 3J illustrates a 2-D planar ultrasonic detector array, FIG. 3K illustrates a 2-D cylindrical array, and FIG. 3L illustrates a 2-D spherical ultrasonic detector array in accordance with some embodiments. Note that FIGS. 3H-3L illustrate a detection FOV associated with each ultrasonic detector array configuration.

Figure 4:
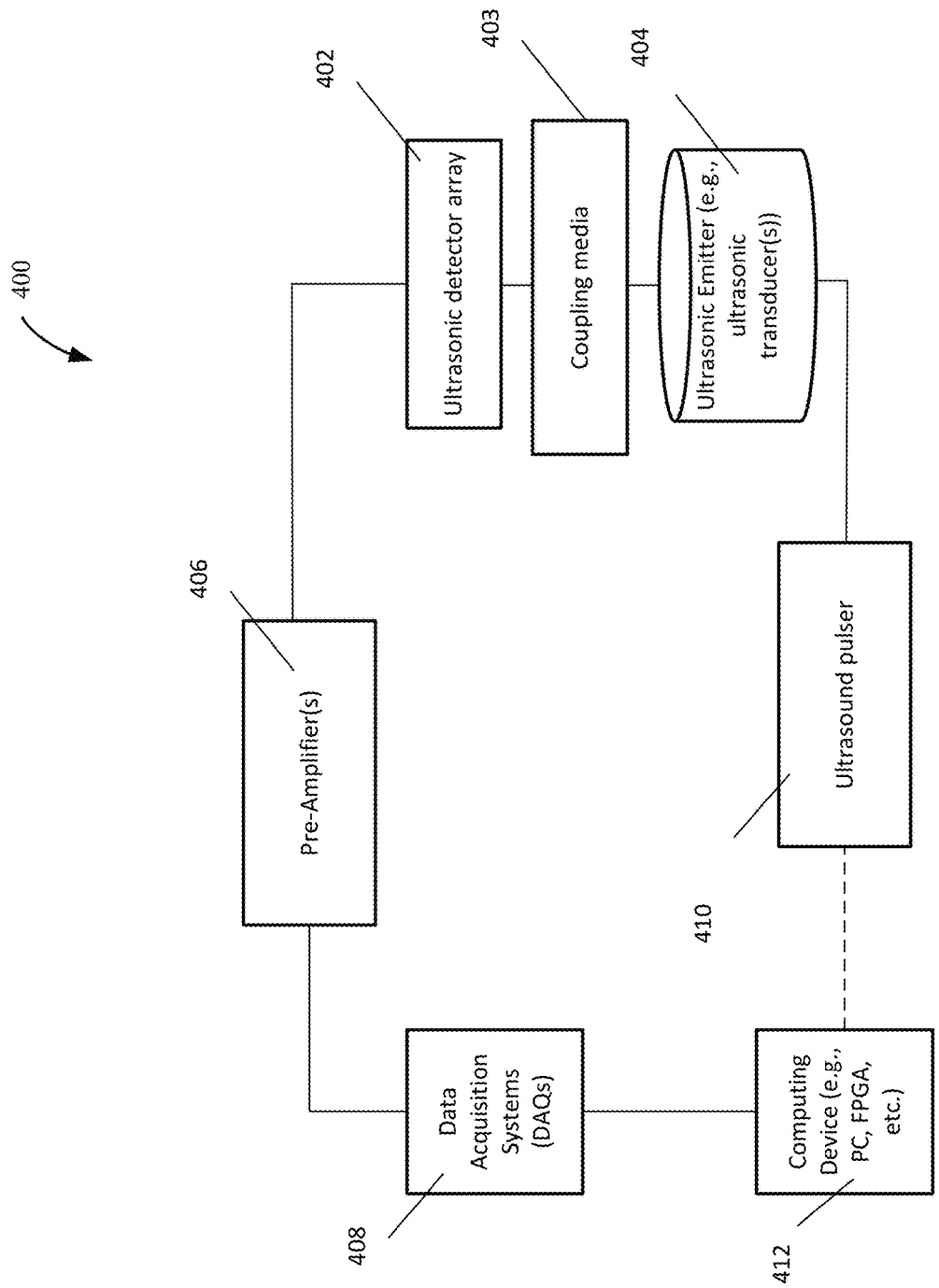
FIG. 4 is a schematic diagram that illustrates components of a Cross-Ray Ultrasound Tomography (CRUST) system in accordance with some embodiments.

FIG. 4 depicts a schematic diagram of a CRUST system 400 in accordance with some embodiments. The CRUST system 400 includes an ultrasonic detector array 402, a coupling media 403, and an ultrasonic emitter 404. The ultrasonic detector array 402 may be in one of the configurations described with respect to FIGS. 3A-3G. The ultrasonic emitter 404 may be in one of the configurations described with respect to FIGS. 3H-3L. The ultrasonic emitter 404 and ultrasonic detector array 402 are in acoustic communication with the coupling media 403. The coupling media 403 may be, for example, an acoustic media such as an acoustic gel, water, or other medium capable of conveying ultrasound pulses. A sample being imaged may be located in the coupling media 403 during an image acquisition operation of the CRUST system 100. The CRUST system 400 also includes an ultrasound pulser 410 in communication with the ultrasonic transducer 404, one or more pre-amplifier(s) 406 in communication with the ultrasonic detector array 402, one or more data acquisition systems (DAQs) 408 in communication with the one or more pre-amplifier(s) 406, and a computing device 412 in communication with the data acquisition system(s) 408 and optionally (denoted by dotted line) in communication with the ultrasound pulser 410.

In some embodiments, a CRUST system includes an ultrasonic emitter that includes one or more transducer elements driven by pulses from an ultrasonic pulser to generate excitation spherical wave(s). In some embodiments, a CRUST system can include an ultrasonic emitter with multiple ultrasound emitter (transducer) elements arranged in various configurations, such as a ring array, a linear array, a two-dimensional array, etc. The ultrasound pulser may be, for example, a high-power pulse generator (e.g., 5077PR from Olympus, Corp.). In one aspect, the ultrasound pulser can fire at a tunable repetition rate for ultrafast large-field excitation. In one example, the tunable repetition rate can be in tuned within a range from about several Hz (e.g., 5 HZ) to dozens of kHz (e.g., 30 kHz). For example, in the examples shown in FIG. 4, the CRUST system 400 includes an ultrasonic emitter 404 (e.g., one or more ultrasonic transducers) and an ultrasonic pulser 410 to drive the ultrasonic emitter 404 to emit spherical waves.

In some embodiments, a CRUST system includes one or more pre-amplifiers in electrical communication with the ultrasonic detector array. The pre-amplifier(s) are configured to amplify radio frequency signals received from the ultrasonic detector array. In one aspect, the ultrasonic detector array is directly connected to the one or more pre-amplifier(s) to amplify the received radio frequency signals before cable noise can degrade the signal-to-noise ratio (SNR).

Each of the one or more pre-amplifiers may be set to a pre-amplifier gain that may be determined by one or more factors. For example, the pre-amplifier gain may be determined based on one or more of a minimum signal-to-noise ratio (SNR) and one or more operating parameters of the data acquisition and processing system components such as analog-to-digital sampling devices (digitizers) of the DAQs, signal amplifiers, buffers, and the computing device. In one aspect, the pre-amplifier gain is in a range that is high enough to enable transmission of the RF signals generated by the ultrasonic detector array with minimal signal contamination, but below a gain that may saturate the dynamic ranges of the DAQ system used to digitize the photoacoustic signals amplified by the pre-amplifier(s). In certain aspects, the gain of the one or more pre-amplifier channels may be at least about 5 dB, at least about 7 dB, at least about 9 dB, at least about 11 dB, at least about 13 dB, at least about 15 dB, at least about 17 dB, at least about 19 dB, at least about 21 dB, at least about 23 dB, at least about 25 dB, or at least about 30 dB.

Returning to FIG. 4, the CRUST system 400 includes an ultrasonic detector array 402 that is directly connected or coupled to pre-amplifier(s) 406. Ultrasonic detector array 402 may be coupled with electrical connecting cables. In one aspect, wireless communication may be employed. In one aspect, the pre-amplifier(s) 406 can amplify radio frequency signals received from the ultrasonic detector array 402 before cable noise degrades the signal-to-noise Ratio (SNR).

In some embodiments, a CRUST system includes one or more data acquisition systems that may include, e.g., data acquisition boards. The data acquisition system(s) are in electrical communication with the pre-amplifier(s). In one aspect, each pre-amplifier is coupled in one-to-one correspondence with one data acquisition system. In some embodiments, with one-to-one mapped analog-to-digital sampling, each pre-amplifier is operatively coupled to a corresponding dedicated data channel of an analog-to-digital sampling device in a DAQ to allow for parallelized analog-to-digital sampling of pre-amplified signals. The pre-amplified signals produced by each individual channel of the pre-amplifier are received by a single dedicated data channel of the at least one analog-to-digital sampling devices. Any suitable number of pre-amplifier devices and/or DAQ devices may be used to provide the one-to-one mapping. For example, a CRUST system may include four 128-channel DAQs (e.g., SonixDAQ made by Ultrasonix Medical ULC with 40 MHz sampling rate, 12-bit dynamic range, and programmable amplification up to 51 dB) in communication with four 128-channel pre-amplifiers to provide simultaneous one-to-one mapped associations The amplified radio frequency signals output from the one or more pre-amplifiers can be digitized by one or more data acquisition system(s). In some embodiments, the data acquisition systems can record radio frequency signals at time intervals defined by a sampling frequency. For example, in FIG. 4, the CRUST system 400 includes one or more data acquisition systems 408 in electrical communication with the pre-amplifier(s) 406 to digitize the amplified radio frequency signals output from the pre-amplifier(s) 406.

In some embodiments, a CRUST system includes a computing device. In some aspects, the computing device includes a non-transitory computer readable media (CRM)

and one or more processors in communication with the non-transitory computer readable media. The computing device may be in electrical communication with one or more data acquisition systems and/or in electrical communication with other system components such as an ultrasound pulser, and/or one or more pre-amplifiers (e.g., to send control signal(s) to adjust a gain, etc.). Communication between the computing device and various components of the CRUST system may be in wired and/or wireless form. Additionally, one or more of the electrical communications between components of the CRUST system may be able to provide power in addition to communicate signals.

For example, the computing device may receive acoustic data from the data acquisition system(s). The computing device can include instructions (e.g., stored in CRM) for performing operations for signal processing, image reconstruction, and/or image processing. For example, the computing device can be a device capable of performing various signal processing techniques required for reconstructing scattering coefficients whose distribution forms an ultrasonic tomographic image, calculating Doppler frequency shifts when performing PDI, performing any suitable pre-processing or post-processing of recorded RF signals, etc. In some embodiments, the computing device can perform operations of the methods of the flowcharts illustrated in FIGS. 6 and 10.

Some examples of a computing device of a CRUST system include a desktop computer, a laptop computer, a Field Programmable Gate Array (FPGA), an embedded computer, a single board computer (e.g, Raspberry Pi or similar), a controller, or any other computation device or system of devices capable of performing the functions described herein.

In some aspects, the computing device can include or be associated with one or more input devices for setting parameters for image acquisition, for setting parameters for ultrasonic emitter and/or ultrasonic detector array, for setting parameters for DAQ(s), etc. For example, the input devices can include a keyboard, a mouse, a trackpad, etc. Additionally, in some embodiments, the computing device can include one or more output devices. For example, the one or more output devices can be used to present an ultrasonic tomographic image, present PDI images, present audio sounds associated with an imaging technique, etc. Example output devices include a display screen, speakers, etc. Input and output devices of the computing device can be in communication with a processor of the computing device Returning to FIG. 4, the CRUST system 400 includes a computing device 412 (e.g., PC, FPGA, etc.) in electrical communication with the DAQs 408 to receive acoustic data. Computing device 412 can be a device suitable for signal processing, image reconstruction, and/or image processing. For example, computing device 412 can be a device capable of performing various signal processing techniques required for reconstructing scattering coefficients whose distribution forms an ultrasonic tomographic image, calculating Doppler frequency shifts when performing PDI, performing any suitable pre-processing or post-processing of recorded RF signals, etc. In one aspect, computing device 412 can perform operations of one or both of the methods depicted by the flowcharts illustrated in FIGS. 6 and 10.

Computing device 412 may be, for example, a desktop computer, a laptop computer, a Field Programmable Gate Array (FPGA), a single board computer (Raspberry Pi or similar), a controller, an embedded computer, etc. In some embodiments, computing device 412 may include or be associated with one or more input devices (e.g., keyboard, mouse, trackpad, etc.) for setting parameters for image acquisition, for controlling or otherwise setting parameters for various system components such as, for example, the ultrasonic transducer 404, the ultrasonic detector array 402, and/or the DAQs 408. Alternatively or additionally, computing device 412 may include one or more output devices. For example, the one or more output devices can be used to output one or more ultrasonic tomographic images, PDI images, audio sounds associated with an imaging technique, etc. Example output devices include a display screen, speakers, etc.

In some embodiments, a CRUST system can include one or more communication interfaces (e.g., a universal serial bus (USB) interface). Communication interfaces can be used, for example, to connect various peripherals and input/output (I/O) devices such as a wired keyboard or mouse or to connect a dongle for use in wirelessly connecting various wireless-enabled peripherals. Such additional interfaces also can include serial interfaces such as, for example, an interface to connect to a ribbon cable. It should also be appreciated that the various system components can be electrically coupled to communicate with various components over one or more of a variety of suitable interfaces and cables such as, for example, USB interfaces and cables, ribbon cables, Ethernet cables, among other suitable interfaces and cables.

FIG. 5 depicts a schematic diagram of components of a CRUST system 500 in accordance with some embodiments. In the illustrated example, the CRUST system 500 includes an ultrasonic emitter 504 that is a single-element spherically focused transducer. In one aspect, the ultrasonic emitter 504 is a 5-MHz spherically focused transducer capable of 5 MHz transmission of spherical acoustic wave waves. The CRUST system 500 also includes an ultrasonic detector array 502 that is a ring array (i.e., a curved 1-D array) with a detector focal plane 503. The ultrasonic detector array 502 is configured for elevationally focusing for detection. In one aspect, the ultrasonic detector array 502 is a 5-MHz, 512-element, 10-cm in diameter, elevationally-focused ultrasonic transducer array. As illustrated, ultrasonic emitter 504 produces a VPS 506 using positive focusing. That is, the focal point associated with ultrasonic emitter 504, and therefore the location of the VPS 506, is along a direction in which the excitation ultrasonic wave/beam 512 from the ultrasonic emitter 504 travels, as shown in FIG. 5. FIG. 5 additionally illustrates a point scatterer 510 that can scatter the excitation ultrasonic wave to generate a side-scattered wave 514 that can be detected by the ultrasonic detector array 502. Additionally, FIG. 5 shows an angle 516 between excitation ultrasonic wave 512 and side-scattered wave 514.

IV. Cross-Ray Ultrasound Tomography (CRUST) methods

Figure 6:
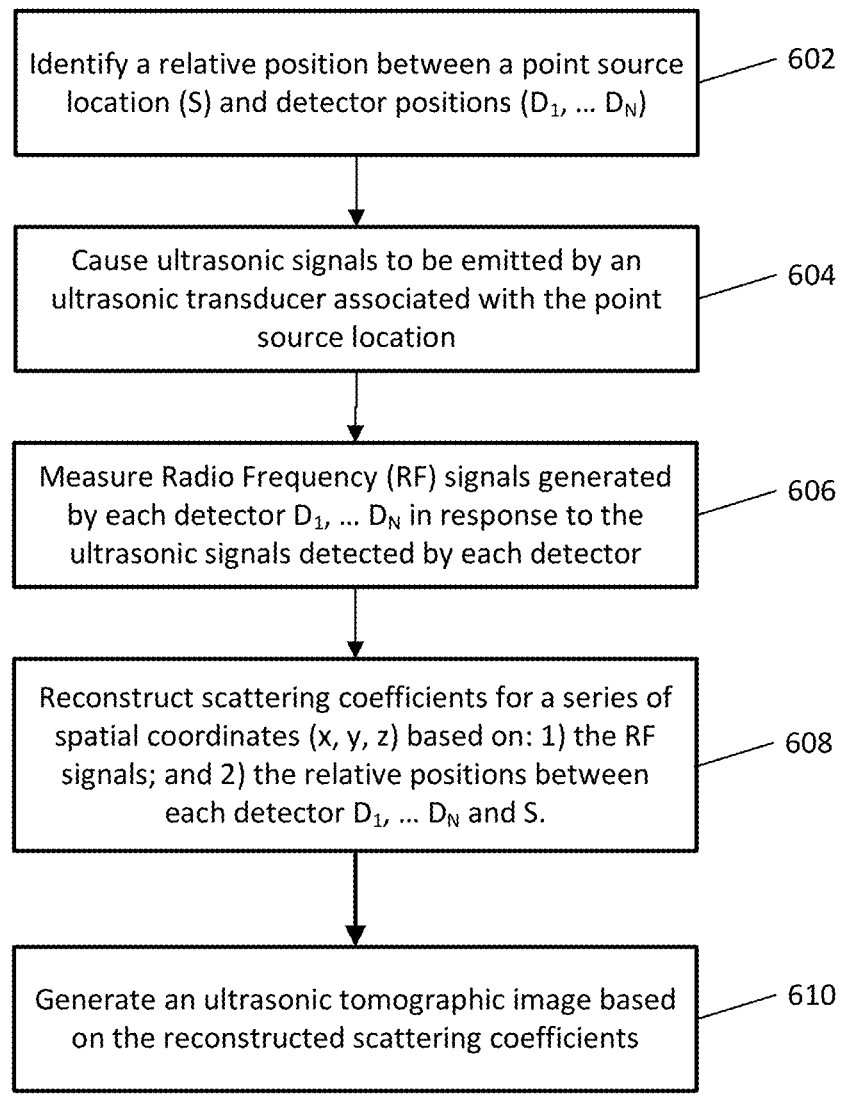
FIG. 6 is an example flowchart illustrating a process for reconstructing one or more tomographic images using a CRUST system in accordance with some embodiments.

FIG. 6 depicts a flowchart 600 of a CRUST method that can be used to reconstruct one or more tomographic images from acoustic data derived from acoustic waves detected by a transducer detector array of a CRUST system in accordance with some embodiments. Note that one or more blocks of the method shown in FIG. 6 can be executed on one or more devices, e.g., on computing device 412 of FIG. 4. Additionally, note that blocks of method 600 can be performed in various orders, and some of the blocks of method 600 may be omitted in some embodiments.

At 602, a relative position between a point source location (S) of, for example, an ultrasonic emitter (transducer(s)) and one or more positions (locations) of N detectors ($D_1, \ldots D_N$) in an ultrasonic detector array are identified. As described above in connection with FIGS. 1, 2, and 3, the point source can be either a physical point source of an ultrasonic emitter such as a single element ultrasonic transducer or a VPS that is at a focal point of one or more transducer elements in, for example, a 1-D or 2-D array of transducer elements. Additionally, as shown in and described above in connection with FIG. 3, each detector $D_1, \ldots D_N$ can be part of an ultrasonic detector array that can be arranged in a variety of 1-D and 2-D configurations.

Note that although the detectors in the ultrasonic detector array are generally referred to herein as $D_1, \ldots D_N$, it should be understood that N can be any suitable integer greater than or equal to 1.

In some embodiments, the relative position between the point source location (S) and the detector positions $(D_1, \ldots D_N)$ can be determined via a calibration technique. For example, the relative position can be determined by identifying a focal point of one or more ultrasonic transducer(s) of the ultrasound emitter using a point scatter as a target, where the focal point corresponds to the location of the VPS and the corresponding point source S. The relative position between the focal point determined and each of the detector (transducer) locations $(D_1, \ldots D_N)$ on the ultrasonic detector array can then be determined. More detailed techniques for identifying the relative position between the point source location (S) and the detector positions $(D_1, \ldots D_N)$ are shown in and described below in connection with FIG. 7.

At 604, ultrasonic signals can be caused to be emitted by the one or more ultrasonic transducers of the ultrasonic emitter where the one or more ultrasonic transducers are associated with the point source location S. For example, a computing device can instruct a pulse generator to generate ultrasonic pulses. The pulse generator is coupled to or in communication with the ultrasonic emitter to transmit the ultrasonic pulses to the ultrasonic emitter causing ultrasonic waves to be emitted. In some embodiments, the instructions can include various parameters of the ultrasonic signals, such as a pulse frequency, a pulse amplitude, a pulse duration, a number of pulses, a total duration of a pulse burst, etc. Note that an example of a CRUST system that includes a computing device, a pulse generator, and an ultrasonic emitter is shown in and described above in connection with FIG. 4.

At 606, one or more RF signals generated by each detector $D_1, \ldots D_N$ are measured. In some embodiments, each detector of the ultrasonic detection array can generate one or more RF signals based on detected ultrasonic waves, e.g., from waves scattered by the target. That is, each detector can convert detected ultrasonic waves to one or more RF signals. In some embodiments, the one or more RF signals can be amplified by one or more pre-amplifiers coupled to the ultrasonic detector array, as shown in and described above in connection with FIG. 4. In some embodiments, the RF signals and/or the amplified RF signals can be captured and stored by a computing device via a DAQ board, as shown in and described above in connection with FIG. 4.

At 608, scattering coefficients for a series of spatial coordinates (x, y, z) can be reconstructed based on: 1) the one or more RF signals measurements; and 2) the relative positions between the point source S and each detector $D_1, \ldots D_N$ of the detector array In one aspect, the scattering coefficients can be reconstructed using equation 5 above.

At 610, one or more ultrasonic tomographic images can be generated based on a distribution of the reconstructed scattering coefficients. For example, an ultrasonic tomographic image can be generated such that each pixel of the image corresponds to the value of the scattering coefficients at a corresponding spatial coordinate.

In some embodiments, the ultrasonic tomographic image can be presented on a display screen, such as a display screen of a computing device used to control a pulse generator coupled to the ultrasonic transducer and/or a computing device used to receive RF signals generated by the ultrasonic detector array, as shown in and described above in connection with FIG. 4.

A. Example Calibration Method

As described above, CRUST can be implemented by a CRUST system of one of various configurations of ultrasonic emitters and ultrasonic detectors. In certain aspects, a CRUST system can be calibrated for one or more specific configurations of ultrasonic emitters and ultrasonic detectors being used and/or for a specific application. For example, a CRUST system may be calibrated to identify the focal point of an ultrasonic emitter corresponding to a location of a VPS implemented by the CRUST system.

Figure 7:
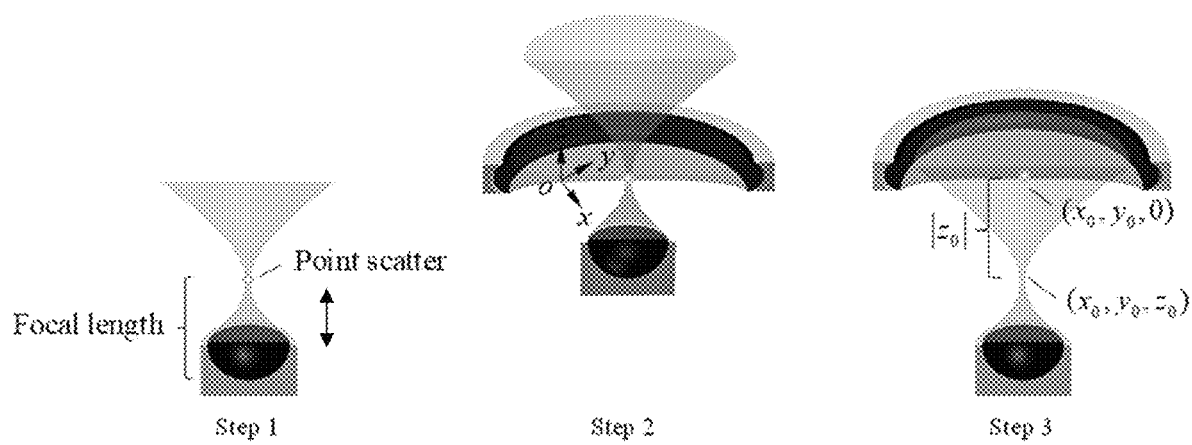
FIG. 7 is a schematic diagram illustrating a method for calibration of a CRUST system in accordance with some embodiments.

FIG. 7 schematically illustrates steps of a calibration technique that can be used to calibrate a CRUST system in accordance with some embodiments. Note that although the diagrams shown in FIG. 7 illustrate a CRUST system with an ultrasonic transmitter (emitter) in the form of a spherical ultrasonic transmitter (transducer) and an ultrasonic detector array in the form of a full ring array of elevationally focused transducers, the steps illustrated in FIG. 7 can be used to calibrate a CRUST system having any suitable emitter and/or detector array configuration(s). The CRUST system illustrated in FIG. 7 includes a reference coordinate system at origin O. The calibration technique can be used to identify the spatial coordinates $(x_0, y_0, z_0)$ of the focal point of an ultrasonic transmitter.

As illustrated, at step 1, the approximate x-coordinate and y-coordinate of the focal point of the ultrasonic transmitter can be identified by moving (in the x-direction and in the y-direction) a point scatter target in front of the ultrasonic transmitter (emitter) until the point scatter target is at a location where the maximum echo amplitude is found using a pulse-echo mode of the ultrasonic emitter. Note that the point scatter target can be a target such as a small metal ball, a small air bubble, etc. Although the illustrated example shows the ultrasonic detector array omitted from the CRUST system during this step, in other examples, the ultrasonic detector array may remain. The ultrasonic transmitter may be in communication with a computing device at least during the calibration step to measure the RF signal from the ultrasonic transmitter to determine the maximum echo amplitude. Alternatively, the ultrasonic transmitter may measure the maximum echo amplitude.

At step 2, the point scatter target and the ultrasonic transmitter (emitter) are moved as a whole to, or approximately to, a focal plane or imaging plane of the ultrasonic detector array and the point scatter target and focal point are approximately at the center of the ultrasonic detector array. For example, at step 2 in FIG. 7, the point scatter target and the ultrasonic transmitter are moved as a whole to the focal plane of the elevationally focused full ring array being used as an ultrasonic detector array. In addition or alternatively, the ultrasonic detector array may be located/moved such that point scatter target and focal point of the ultrasonic transmitter are in, or approximately in, the focal plane of the ultrasonic detector array and approximately at the center of the ultrasonic detector array. At step 2, the point scatter target and the ultrasonic transmitter are moved together (additionally or alternatively the ultrasonic detector array is moved) along the z-axis until a maximum scattering signal is detected by the detectors (transducers) of the ultrasonic detector array. At this point, the point scatter has been placed in the imaging focal plane of the ultrasonic detector array. The z-location of the focal point is z=0 when the maximum scattering signal is detected by the ultrasonic detector array.

In the illustrated example, the imaging focal (imaging) plane of the ultrasonic detector array is defined by an x-y plane and a z-axis orthogonal to the x-y plane.

At step 3, while maintaining the location of the point scatter target, the ultrasonic transmitter is moved away from the ultrasonic detector array along the z direction by a distance of $|z_0|$, e.g., 5 cm. Additionally or alternatively, the ultrasonic detector array may be moved. When the relative distance between the ultrasonic detector array and the ultrasonic transmitter is of $|z_0|$, the ultrasonic transmitter emits ultrasonic waves and the ultrasonic detector array detects ultrasonic signals scatter by the point scatter target. An image is reconstructed from the acoustic data from the RF signals generated by the ultrasonic detector array. Because the ultrasonic transmitter's focal point shares the same x and y coordinates (i.e. $x_0$ and $y_0$) with those of the point scatter target, the focal point x- and y-coordinates can be extracted from the reconstructed image of the point scatter target, as depicted in step 3 of FIG. 7.

Figure 8:
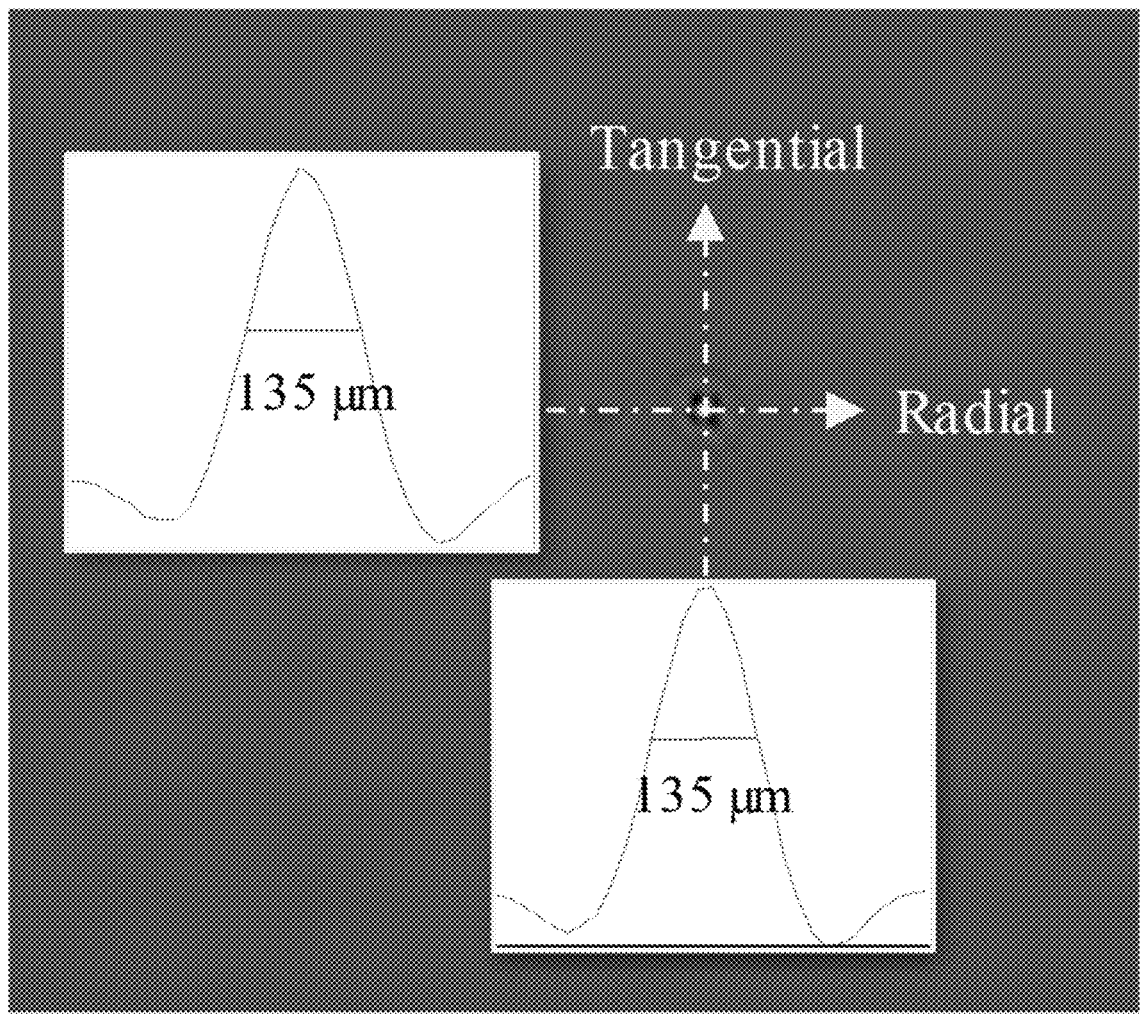
FIG. 8 illustrates plots of point spread function along tangential and radial directions, according to an aspect.

FIG. 8 shows two plots of point spread function (PSF) of the CRUST system illustrated in FIG. 5 after performing the calibration technique shown in and described above in connection with FIG. 7. As illustrated, the Full Width Half Maximum (FWHM), which represents the spatial resolution of the example CRUST system, was measured to be 135 μm along both the tangential and radial directions.

B. CRUST Method with Power Doppler Imaging

A CRUST system of certain embodiments can be used to perform power Doppler imaging (PDI). PDI has a higher sensitivity than conventional color Doppler imaging for detecting flow, and is particularly useful for imaging small vessels and vessels with low-velocity flows.

When using a CRUST system, PDI can be performed by implementing an ultra-high frame rate, typically above 1 kHz. Each frame can be reconstructed using the back-projection algorithm described above in connection with FIGS. 2 and 6.

In general, the pixel values $I_{PDI}$ in a final PDI image is computed from the set of reconstructed frames as follows:

$$I_{PDI} = \frac{1}{M}\sum_{i=1}^{M} A_i^2 \quad \text{(Eqn. 6)}$$

In equation 6 above, M represents the number of frames used for PDI calculation, and $A_i$ stands for the pixel value fluctuation after a clutter filtration technique is applied to the $i^{th}$ frame. An example technique for performing clutter filtration is described in Charlie Demené, Thomas Deffieux, Mathieu Pernot, Bruno-Félix Osmanski, Valérie Biran, Jean-Luc Gennisson, Lim-Anna Sieu, Antoine Bergel, Stéphanie Franqui, Jean-Michel Correas, Ivan Cohen, Olivier Baud, and Mickael Tanter. "Spatiotemporal clutter filtering of ultrafast ultrasound data highly increases Doppler and Ultrasound sensitivity." IEEE transactions on medical imaging 34.11 (2015): 2271-2285, which is incorporated by reference herein in its entirety.

Vector Velocity Estimation

Figure 9:
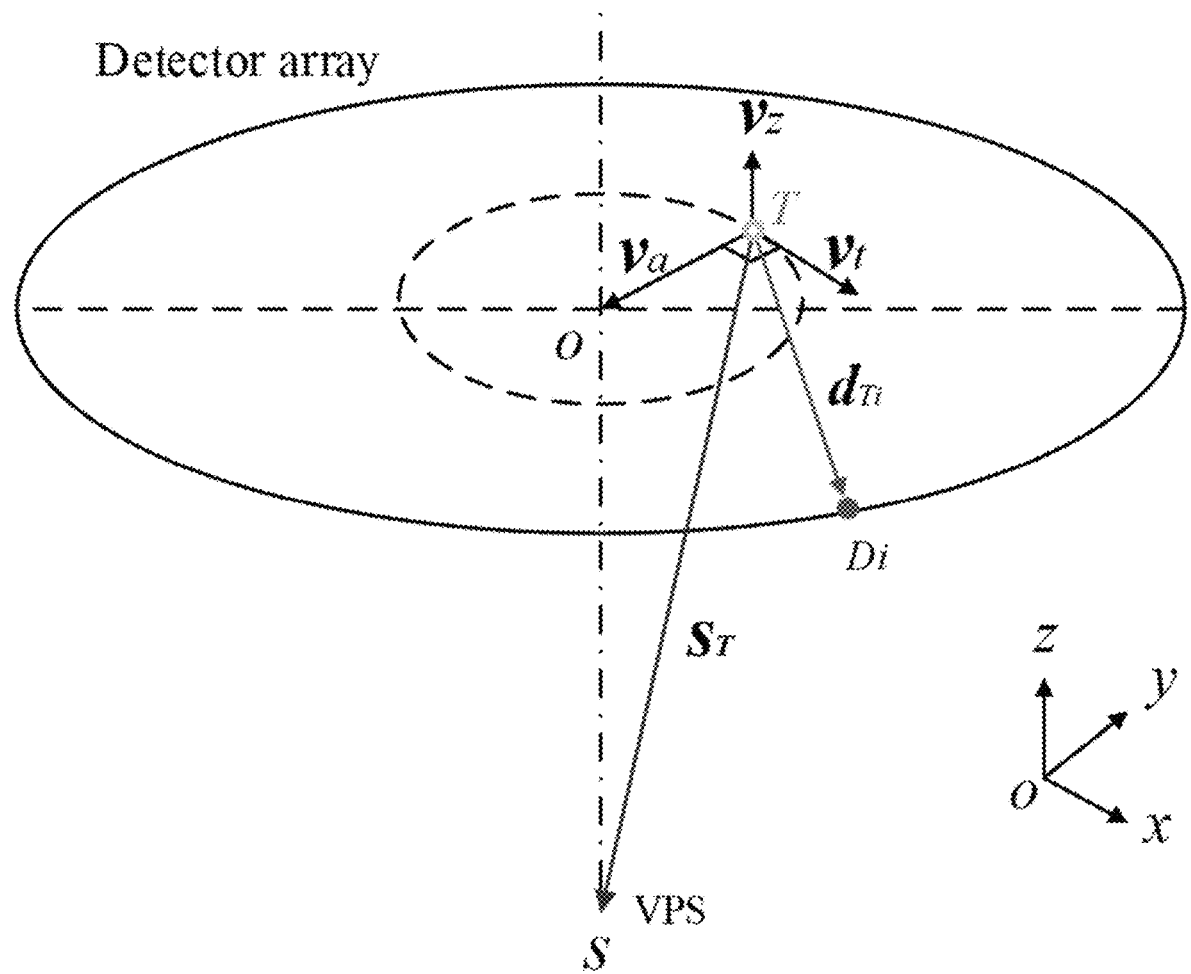
FIG. 9 is a schematic drawing of points of interest for calculating a flow velocity vector for power Doppler imaging in accordance with some embodiments.

FIG. 9 illustrates a schematic diagram of the CRUST system depicted in FIG. 5. The notations in FIG. 9 will be used below in describing techniques for calculating a velocity flow vector for a pixel of a PDI image.

In the imaging focal plane, $v_a$ is defined as a unit vector in the direction of T to O. Unit vector $v_t$ is defined as originating from T and counterclockwise (following the right-hand rule with the thumb pointing to the z axis) perpendicular to $v_a$. An out-of-plane unit vector $v_z$ is defined to be aligned with the z axis. Any velocity vector v can therefore be decomposed into $v=av_a+bv_b+gv_z$, where a, b, and g are projection coefficients.

The unit vector in the direction of T to S is defined as $s_T$, and the unit vector in the direction of T to $D_i$ is defined as $d_{Ti}$. The Doppler frequency shift at T observed by detector Di is derived to be:

$$f_{Ti} = \frac{f_0}{c}(v \cdot d_{Ti} + v \cdot s_T) = \frac{f_0}{c}[av_a \cdot (d_{Ti} + s_T) + bv_t \cdot d_{Ti} + gv_z \cdot s_T] \quad \text{(Eqn. 7)}$$

In equation 7 above, $f_0$ is the carrier frequency of the excitation ultrasound. Note that equation 7 is valid when the amplitude of v is much less than c, the speed of sound.

Equation 7 can be rewritten in a matrix notation as:

$$\begin{bmatrix} v_a \cdot (d_{T1} + s_T) & v_t \cdot d_{T1} & v_z \cdot s_T \\ \vdots & \vdots & \vdots \\ v_a \cdot (d_{Ti} + s_T) & v_t \cdot d_{Ti} & v_z \cdot s_T \\ \vdots & \vdots & \vdots \\ v_a \cdot (d_{Tl} + s_T) & v_t \cdot d_{Tl} & v_z \cdot s_T \end{bmatrix} \begin{bmatrix} a \\ b \\ g \end{bmatrix} = \begin{bmatrix} u_1 \\ \vdots \\ u_i \\ \vdots \\ u_l \end{bmatrix} \quad \text{(Eqn. 8)}$$

In equation 8 above, the first term (i.e., the coefficient matrix) can be denoted as H, the second term (i.e., the coefficient vector) can be denoted as v, and the last term can be denoted as u. In u, $u_i$ is defined as $u_i=cf_{Ti}/f_0$.

Note that equation 8 describes an overdetermined system whereby l data values, i.e., frequency shift estimates from all receiving elements, are used as input to solve for three unknowns—radial, tangential, and out-of-plane velocity vector coefficients. Using principles of linear algebra, v can be found by multiplying the pseudo-inverse of H with u, which is also referred to as the least-squares fitting solution. This yields:

$$c = \begin{bmatrix} a \\ b \\ g \end{bmatrix} = (H^T H)^{-1} H^T u \quad \text{(Eqn. 9)}$$

Figure 10:
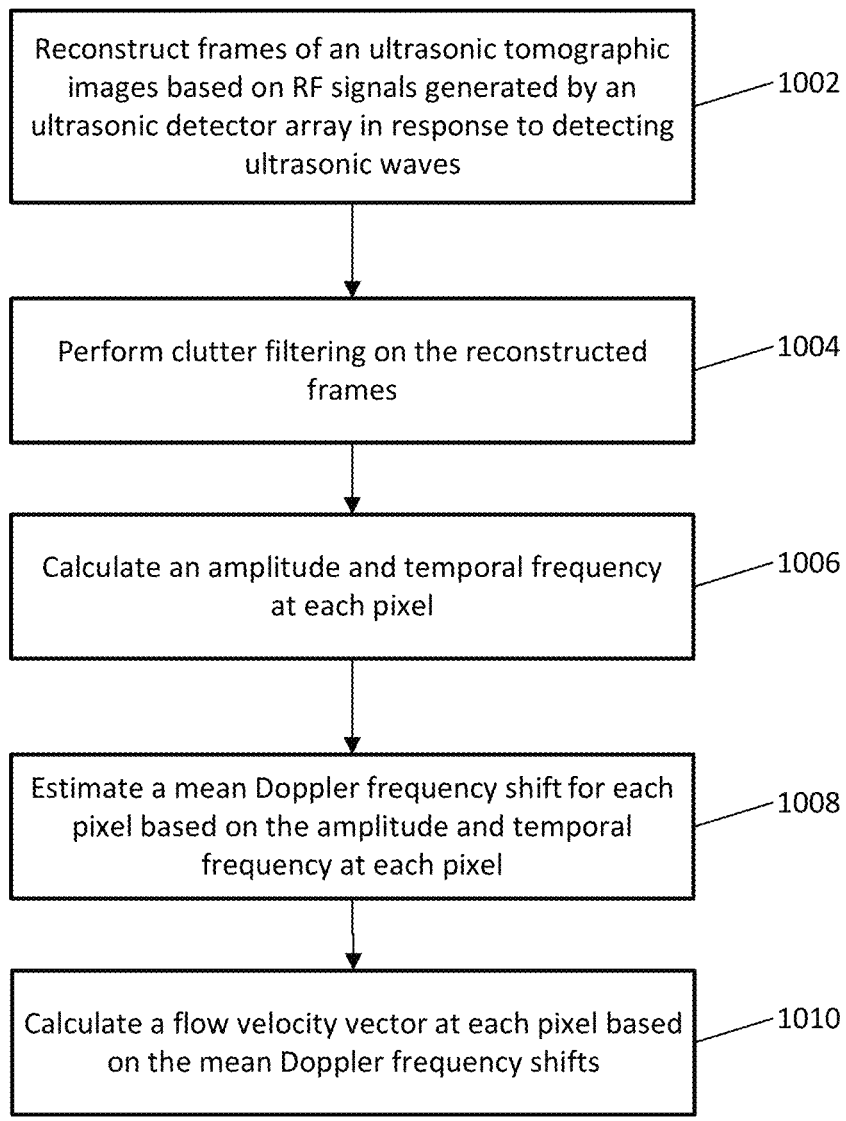
FIG. 10 is an example flowchart illustrating a process for performing power Doppler imaging using a CRUST system in accordance with some embodiments.

FIG. 10 depicts a flowchart 1000 of operations in a CRUST method for performing PDI using a CRUST system in accordance with some embodiments. Note that one or more operations of the method shown in FIG. 10 can be performed by a processor of a computing device, such as computing device 412 as shown in and described above in FIG. 4, or by multiple computing devices. Additionally, the blocks of the flowchart 1000 can be performed in various orders, and some of the blocks of method 1000 may be omitted in some embodiments.

At 1002, frames of ultrasonic tomographic images of a target being imaged can be reconstructed based on RF signals generated by an ultrasonic detector array in response to detecting scattered ultrasonic waves. In some embodiments, each frame can be reconstructed by reconstructing the scattering coefficients for a series of (x, y, z) coordinates using, for example, equation 5 above. For example, the amplitudes of the pixels in each frame can be assigned the reconstructed scattering coefficients at the respective (x, y, z)

coordinates. The reconstructed pixel values for the j-th frame out of m frames is referred to as $A_{pi}(j)$, where each value of $A_{pi}(j)$ is a pixel amplitude that corresponds to a reconstructed scattering coefficient at that pixel location reconstructed using RF signals generated by the $i^{th}$ detector element $D_i$ in frame j. However, in some embodiments, to increase SNR, detector element $D_i$ can be a group of adjacent detectors (e.g., two detectors, five detectors, etc.) with a total length that is substantially smaller than its center distance to the pixel. The group of adjacent detectors is sometimes referred to herein as a subgroup of detectors in the ultrasonic detector array. In some such embodiments, a sliding window of the total element length can be used to select the next group of detector elements for reconstruction. Additionally, the total group number represents the total angles that are used to observe the flow, and is indicated by l in equation 8 above.

At 1004, clutter filtering can be performed on the reconstructed frames. In some embodiments, clutter filtering can be applied individually to the ensembles of pixel values for each reconstructed pixel over multiple reconstructed frames. Clutter filtering can be performed to remove clutter artifacts from reconstructed frames, for example, from reflections from static or slow-moving bones and tissue that are substantially larger in amplitude than backscattered signals from flow. However, it should be noted that in some embodiments, other filtering techniques for removing artifacts from reconstructed frames may be performed in addition to or alternatively to clutter filtering.

At 1006, an amplitude and a temporal frequency can be calculated for each pixel in each clutter filtered frame. The amplitude and temporal frequency can be retrieved from $A_{pi}(j) + i*h_{pi}(j)$, which is an analytical signal of $A_{pi}(j)$, and, $h_{pi}(j)$ can be a Hilbert transform of $A_{pi}(j)$.

In some embodiments, a PDI image can be generated based on the clutter filtered frames using Eqn. 6. In some such embodiments, the PDI image can be presented, for example, on a display screen of a computing device used to reconstruct the PDI image.

At 1008, a mean Doppler frequency shift can be calculated for each pixel based on the amplitude and temporal frequency of that pixel. The estimated mean Doppler frequency shift at each pixel is denoted as $f_{Ti}$ as indicated in Eqn. 7.

In some embodiments, $f_{Ti}$ can be achieved using lag-one autocorrelation based on the analytical signals associated with the amplitudes of a pixel reconstructed in a set of m frames. In particular, the lag-one correlation of an analytical signal can be expressed as:

$$R_{pi}(1) = \sum_{j=1}^{m}(A_{pi}(j) + i*h_{pi}(j))\overline{(A_{pi}(j-1) + i*h_{pi}(j-1)} \quad \text{(Eqn. 10)}$$

In Eqn. 10, the second term of the summation denotes the complex conjugate of the analytical signal at frame j−1.

The mean phase shift $\bar{\omega}$ between adjacent frames at each pixel over m frames can be achieved by calculating the phase of $R_{pi}(1)$ through $$\bar{\omega} = \tan^{-1}\left(\frac{\text{Im}(R_{pi}(1))}{\text{Re}(R_{pi}(1))}\right).$$

Denoting the frame rate as $f_s$, $f_{Ti}$ can then be calculated by $$f_{Ti} = f_s \frac{\bar{\omega}}{2\pi}.$$

In some embodiments, the mean frequency estimates can be regularized. For example, in some embodiments, pixels with an intensity below a threshold can be removed from consideration in the mean frequency estimate. In other words, in some embodiments, only pixels with an intensity above the threshold can be included in the mean frequency calculation. This can effectively avoid spurious mean frequency estimates due to noise, while also reducing computational cost. As another example, in some embodiments, unwrapping can be performed to account for possible aliasing artifacts generated in performing the lag-one autocorrelation.

At 1010, a flow velocity vector can be calculated at each pixel based on the mean Doppler frequency shifts. Note that the flow velocity vector is the vector v described above in connection with equations 7-9 above. Accordingly, the flow velocity vector can be calculated by solving equation 9 above, and using $u_i = cf_{Ti}/f_0$, where $f_{Ti}$ is the calculated mean Doppler frequency shift observed by detector $D_i$ or a subgroup of detectors.

Experimental PDI Results Using a CRUST System

Figure 11:
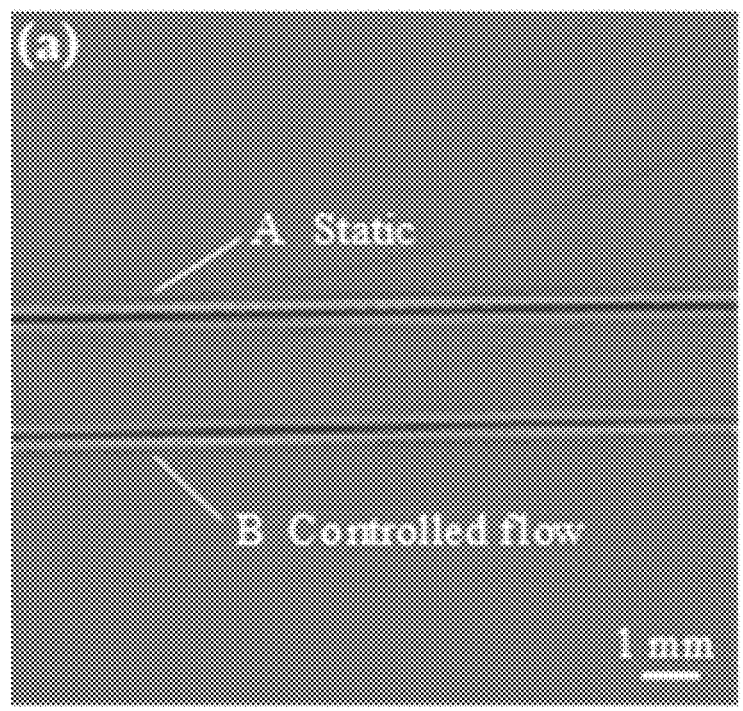
FIG. 11 illustrates an experimental setup for power Doppler imaging using a CRUST system, according to an aspect.
Figure 12F:
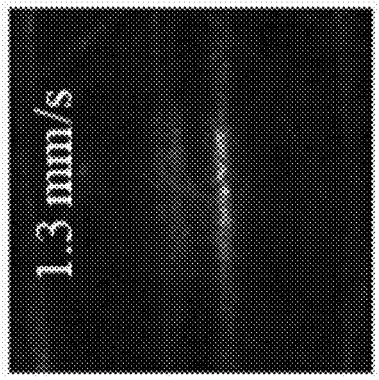
Figure 12H:
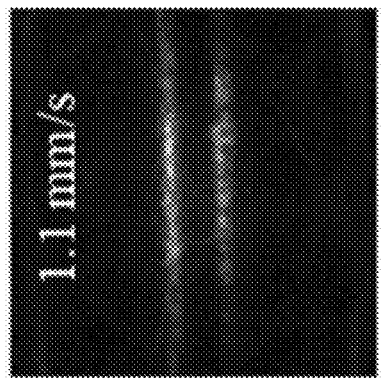
Figure 12E:
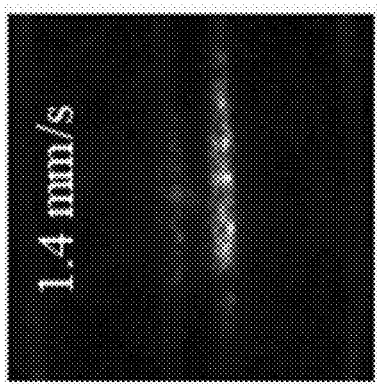
Figure 12G:
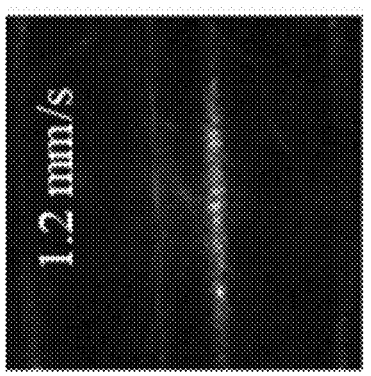

FIG. 11 illustrates an experimental setup for performing PDI using the CRUST system depicted in FIG. 5.

PDI was performed using a 5-MHz spherically focused transducer for ultrasound transmission, and a 5-MHz 512-element, 10-cm-in-diameter elevationally focused full-ring transducer array for detection.

In certain aspects, an ultrasonic transducer array of a CRUST system may include a plurality of N transducers (sometimes referred to herein as "transducer elements" or "emitters") operable to collect ultrasonic signals, e.g., in parallel. Each transducer element has an aperture (e.g., a flat-rectangular aperture). The transducer elements have a height, a width, and a pitch. In one case, the pitch is about 1.35 mm In one case, the width is 0.65 mm In another case, the pitch is in a range of 1.20 mm to 1.50 mm. In another case, the height is about 5 mm. In another case, the height is in a range of 2 mm to 10 mm. The N transducer elements may be arranged in 1-D array or a 2-D array or a combination of 1-D arrays and/or 2-D arrays. For example, the transducers may be arranged in a circular array such as a full-ring array. In some cases, more than one array may be used. In one example, a full-ring ultrasonic array is employed to be able to provide panoramic detection. In this case, the full-ring ultrasonic array (e.g., a 512-element full-ring ultrasonic transducer) includes transducer elements distributed along the circumference of a ring having a diameter and an inter-element spacing. The ring diameter may be at least 220 mm in one aspect, may be at least 200 mm in one aspect, or may be at least 250 mm in one aspect. In one aspect, the ring diameter is in a range of about 150 mm to about 400 mm. The inter-element spacing may be less than or equal to about 1.0 mm in one aspect, less than or equal to 0.7 mm in one aspect, less than or equal to 1.5 mm in one aspect, or less than or equal to 2.0 mm in one aspect. In one aspect, the inter-element spacing is in a range of 0 mm to about 5 mm In certain aspects, an ultrasonic emitter (sometimes referred to herein as "ultrasonic emitter") of a CRUST system may include one transducer element or a plurality of N transducers to emit ultrasonic waves. In some cases, such as in a calibration operation, the ultrasonic emitter may also detect ultrasonic signals. In one aspect, the ultrasonic emitter includes a single ultrasonic transducer. In another aspect, the ultrasonic emitter includes a plurality of ultrasonic transducers.

Two tubes were filled with blood mimicking fluid (BMF). Referring to FIG. 11, tube A was filled with static solution, and tube B was filled with solution that had a controlled flow velocity. Both tubes were imaged at a 1-kHz frame rate.

FIGS. 12A-12H show tomographic images reconstructed using the techniques described above in connection with FIGS. 9 and 10. Each of FIGS. 12A-12H shows PDI images for different flow velocities for the solution in tube B.

The minimum detectable flow velocity was determined by analyzing the means of the PDI amplitudes of the two tubes within dashed boxes 1202 and 1204 of FIG. 12A, for tube A and tube B, respectively. Assuming normal distributions of the pixel amplitudes, the means and their 95% confidence intervals that correspond to ±1.96 times of the standard errors, were compared at different flow velocities. A crossover of the means was found between flow velocities of 1.1 mm/s and 1.2 mm/s, indicating a minimum detectable flow velocity to be between 1.1 mm/s and 1.2 mm/s.

It should be noted that a CRUST system using different transmitter and/or detector configurations, different transducer components, and/or operating at a different frame rate, may have a different minimum detectable flow velocity than that described above and depicted in FIGS. 11 and 12A-12H.

V. Additional Considerations

Modifications, additions, or omissions may be made to any of the above-described embodiments without departing from the scope of the disclosure. Any of the embodiments described above may include more, fewer, or other features without departing from the scope of the disclosure. Additionally, the steps of described features may be performed in any suitable order without departing from the scope of the disclosure. Also, one or more features from any embodiment may be combined with one or more features of any other embodiment without departing from the scope of the disclosure. The components of any embodiment may be integrated or separated according to particular needs without departing from the scope of the disclosure.

It should be understood that certain aspects described above can be implemented in the form of logic using computer software in a modular or integrated manner Based on the disclosure and teachings provided herein, a person of ordinary skill in the art will know and appreciate other ways and/or methods to implement the present invention using hardware and a combination of hardware and software.

Any of the software components or functions described in this application, may be implemented as software code using any suitable computer language and/or computational software such as, for example, Java, C, C#, C++ or Python, LabVIEW, Mathematica, or other suitable language/computational software, including low level code, including code written for field programmable gate arrays, for example in VHDL. The code may include software libraries for functions like data acquisition and control, motion control, image acquisition and display, etc. Some or all of the code may also run on a personal computer, single board computer, embedded controller, microcontroller, digital signal processor, field programmable gate array and/or any combination thereof or any similar computation device and/or logic device(s). The software code may be stored as a series of instructions, or commands on a CRM such as a random access memory (RAM), a read only memory (ROM), a magnetic medium such as a hard-drive or a floppy disk, or an optical medium such as a CD-ROM, or solid stage storage such as a solid state hard drive or removable flash memory device or any suitable storage device. Any such CRM may reside on or within a single computational apparatus, and may be present on or within different computational apparatuses within a system or network. Although the foregoing disclosed embodiments have been described in some detail to facilitate understanding, the described embodiments are to be considered illustrative and not limiting. It will be apparent to one of ordinary skill in the art that certain changes and modifications can be practiced within the scope of the appended claims.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

What is claimed is:

1. A cross-ray ultrasound tomography system, comprising:
an ultrasonic emitter configured to emit one or more ultrasonic waves;
an ultrasonic detector array configured to generate one or more radio frequency signals in response to detecting ultrasonic waves, wherein the ultrasonic emitter and the ultrasonic detector array are configured such that the ultrasonic emitter is outside of a focal plane of the ultrasonic detector array and such that the one or more ultrasonic waves are emitted by the ultrasonic emitter at an angle to the focal plane of the ultrasonic detector array, wherein the focal plane of the ultrasonic detector array is configured at a plane at elements of the ultrasonic detector array; and
a computing device configured to:
calculate a scattering coefficient at each of a plurality of spatial coordinates, wherein the scattering coefficient at each spatial coordinate is calculated using digitized acoustic data based on the one or more radio frequency signals generated by the ultrasonic detector array; and construct one or more tomographic images from the scattering coefficients calculated at the plurality of spatial coordinates.

2. The cross-ray ultrasound tomography system of claim 1, wherein the ultrasonic detector array is separate from the ultrasonic emitter.

3. The cross-ray ultrasound tomography system of claim 1, wherein the angle is (i) in a range from about 60 degrees to about 120 degrees, (ii) in a range from about 70 degrees to about 110 degrees, (iii) in a range from about 80 degrees to about 100 degrees, or (iv) about 90 degrees.

4. The cross-ray ultrasound tomography system of claim 1, wherein the scattering coefficient is calculated at each spatial coordinate using the digitized acoustic data from the one or more radio frequency signals and a relative position between each transducer in the ultrasonic detector array and (i) a physical point source of one or more transducers of the ultrasonic emitter or (ii) a virtual point source at a focal point of the one or more transducers of the ultrasonic emitter.

5. The cross-ray ultrasound tomography system of claim 4, wherein the focal point of the one or more transducers of the ultrasonic emitter is (i) along a direction of wave propagation from the ultrasonic emitter or (ii) along a direction opposite to the direction of wave propagation from the ultrasonic emitter.

6. The cross-ray ultrasound tomography system of claim 4, wherein the ultrasonic emitter is a concave single-element ultrasonic transducer or a convex single-element ultrasonic transducer.

7. The cross-ray ultrasound tomography system of claim 1, wherein the ultrasonic detector array is a linear array or a two-dimensional array.

8. The cross-ray ultrasound tomography system of claim 1, further comprising one or more pre-amplifiers in communication with the ultrasonic detector array.

9. The cross-ray ultrasound tomography system of claim 1, further comprising an ultrasound pulse generator for driving the ultrasonic emitter to emit the one or more ultrasonic waves.

10. The cross-ray ultrasound tomography system of claim 1, wherein the one or more ultrasonic waves emitted by the ultrasonic emitter cross with one or more side-scattered signals emitted by a scattering object, wherein the one or more side-scattered signals are detected by the ultrasonic detector array.

11. A cross-ray ultrasound tomography method, comprising:
    causing one or more ultrasonic waves to be emitted by an ultrasonic emitter in a direction at an angle to a focal plane of an ultrasonic detector array, wherein the ultrasonic emitter is outside of the focal plane of the ultrasonic detector array, wherein the focal plane of the ultrasonic detector array is configured at a plane at elements of the ultrasonic detector array;
    digitizing one or more radio frequency signals generated by the ultrasonic detector array to generate digitized acoustic data; and
    forming one or more tomographic images by calculating a scattering coefficient at each of a plurality of spatial coordinates using the digitized acoustic data.

12. The cross-ray ultrasound tomography method of claim 11, further comprising:
    calculating a relative position between each transducer in the ultrasonic detector array and (i) a physical point source of one or more transducers of the ultrasonic emitter or (ii) a virtual point source at a focal point of the one or more transducers of the ultrasonic emitter; and
    using the relative position calculated and the digitized acoustic data to calculate the scattering coefficient at each of the plurality of spatial coordinates.

13. The cross-ray ultrasound tomography method of claim 12, further comprising identifying the physical point source or the virtual point source using a beamforming technique.

14. The cross-ray ultrasound tomography method of claim 11, wherein the one or more ultrasonic waves emitted by the ultrasonic emitter are driven by ultrasonic pulses.

15. The cross-ray ultrasound tomography method of claim 11, wherein the angle is (i) in a range from about 60 degrees to about 120 degrees, (ii) in a range from about 70 degrees to about 110 degrees, (iii) in a range from about 80 degrees to about 100 degrees, or (iv) about 90 degrees.

16. A method for quantifying flow velocity, the method comprising:
    identifying a point source location associated with an ultrasonic emitter and a plurality of locations for a plurality of ultrasonic detectors, wherein the ultrasonic emitter and the plurality of ultrasonic detectors are configured such that the ultrasonic emitter is outside of a focal plane of the plurality of ultrasonic detectors and such that ultrasonic waves are emitted in a direction at an angle to a direction from which ultrasonic waves are detected, wherein the focal plane of the plurality of ultrasonic detectors is configured at a plane at elements of the plurality of ultrasonic detectors;
    causing ultrasonic signals to be emitted by the ultrasonic emitter;
    digitizing one or more radio frequency signals generated by the plurality of ultrasonic detectors;
    constructing a plurality of frames of tomographic images based on the digitized one or more radio frequency signals;
    clutter filtering the plurality of frames of tomographic images;
    calculating amplitude and temporal frequency at each of a plurality of pixels of each frame in the clutter-filtered plurality of frames of tomographic images;
    calculating a Doppler frequency shift at each of the plurality of pixels based on the amplitude and temporal frequency calculated at each pixel in the clutter-filtered plurality of frames of tomographic images; and
    calculating a flow velocity vector at each of the plurality of pixels based on the Doppler frequency shift calculated at each of the plurality of pixels.

17. The method of claim 16, wherein the ultrasonic emitter is located separately from the plurality of ultrasonic detectors.

18. The method of claim 16, further comprising generating at least one power Doppler image based on the clutter-filtered plurality of frames of tomographic images.

19. The method of claim 16, wherein the Doppler frequency shift at each pixel is calculated based on an auto-correlation of the amplitude and temporal frequency of each pixel over a series of frames of tomographic images.

20. The method of claim 16, wherein calculating the flow velocity vector at each of the plurality of pixels is based on a least squares fitting of a velocity detected by a subgroup of the plurality of ultrasonic detectors.

* * * * *